US011551806B2

(12) United States Patent
Bess et al.

(10) Patent No.: US 11,551,806 B2
(45) Date of Patent: *Jan. 10, 2023

(54) SYSTEMS AND METHODS FOR INTEGRATING COMMUNICATIONS IN A HEALTHCARE NETWORK

(71) Applicant: 4MEDICA, INC., Marina Del Rey, CA (US)

(72) Inventors: Adam Bess, Beverly Hills, CA (US); Oleg Bess, Beverly Hills, CA (US)

(73) Assignee: 4MEDICA, INC., Marina Del Rey, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,873

(22) Filed: Sep. 27, 2021

(65) Prior Publication Data

US 2022/0013215 A1    Jan. 13, 2022

Related U.S. Application Data

(63) Continuation of application No. 16/107,613, filed on Aug. 21, 2018, now Pat. No. 11,158,418.

(51) Int. Cl.
*G16H 30/20* (2018.01)
*G16H 10/60* (2018.01)
*G06N 20/00* (2019.01)

(52) U.S. Cl.
CPC .............. *G16H 30/20* (2018.01); *G06N 20/00* (2019.01); *G16H 10/60* (2018.01)

(58) Field of Classification Search
CPC .......... G16H 30/20; G16H 10/60; G06N 20/00

USPC ............................................................. 705/3
See application file for complete search history.

(56) References Cited

U.S. PATENT DOCUMENTS

| | | | | |
|---|---|---|---|---|
| 8,515,777 | B1* | 8/2013 | Rajasenan | G16H 40/20 |
| | | | | 705/2 |
| 10,483,003 | B1* | 11/2019 | McNair | G16H 10/60 |
| 10,496,788 | B2* | 12/2019 | Amarasingham | G16H 50/50 |
| 10,593,426 | B2* | 3/2020 | Amarasingham | G16H 50/50 |
| 10,701,210 | B2* | 6/2020 | Bulut | G16H 40/20 |
| 10,734,115 | B1* | 8/2020 | McNair | G16H 50/30 |
| 11,087,874 | B2* | 8/2021 | Campbell | G06Q 10/06398 |
| 11,114,197 | B2* | 9/2021 | Griffin | G16H 10/60 |
| 11,126,627 | B2* | 9/2021 | Corbin | G06Q 10/10 |

(Continued)

OTHER PUBLICATIONS

U.S. Appl. No. 16/107,613, Notice of Allowance dated Jun. 28, 2021, 10 pgs.

(Continued)

*Primary Examiner* — Tauqir Hussain
(74) *Attorney, Agent, or Firm* — Kwan & Olynick LLP

(57) ABSTRACT

An electronic healthcare system for delivering medical services is described. The electronic healthcare systems can includes modules for accessing patient electronic medical records and ordering medical services, which involve HL7 communications between disparate healthcare organizations. The communications can involve custom communication interfaces which are used to parse and translate HL7 messages. Methods and apparatus are described for generating the custom communications interfaces. In one embodiment, the custom communication interfaces can be generated using machine learning algorithms trained to recognize various data types in message segments contained in HL7 messages.

20 Claims, 10 Drawing Sheets

(56) References Cited

U.S. PATENT DOCUMENTS

| | | | | |
|---|---|---|---|---|
| 11,158,418 B2* | 10/2021 | Bess | ................. | G16H 10/60 |
| 11,257,587 B1* | 2/2022 | D'Angelo | ............ | A61B 5/0022 |
| 11,276,501 B1* | 3/2022 | Brook | ................... | G16H 50/70 |
| 11,348,667 B2* | 5/2022 | Hoffman | ............... | G16H 10/60 |
| 11,398,310 B1* | 7/2022 | McNair | ................. | G16H 50/30 |
| 11,399,721 B2* | 8/2022 | Mahalingam | ......... | G16H 10/60 |
| 2008/0021709 A1* | 1/2008 | Greer | .................... | G16H 40/20 |
| | | | | 704/258 |
| 2011/0009707 A1* | 1/2011 | Kaundinya | ............ | G16H 40/67 |
| | | | | 600/300 |
| 2016/0034641 A1* | 2/2016 | Antony | ................. | G16H 10/60 |
| | | | | 705/3 |
| 2016/0063209 A1* | 3/2016 | Malaviya | ............... | G16H 50/30 |
| | | | | 706/12 |
| 2018/0137244 A1* | 5/2018 | Sorenson | ............... | G16H 30/20 |
| 2019/0156484 A1* | 5/2019 | Nye | ....................... | G16H 50/20 |
| 2019/0164285 A1* | 5/2019 | Nye | ....................... | G16H 10/60 |
| 2020/0066392 A1 | 2/2020 | Bess et al. | | |

OTHER PUBLICATIONS

Catriona Waddington, HLSP and Dominique Egger, Integrated Health Services—What and Why? Main Messages; Technical Brief No. 1, May 2008.

Harrison, R. Integrated Health Care Literature Review.

Saddique, A.A. Integrated Delivery Systems (IDSs) as a Means of Reducing Costs and Improving Healthcare Delivery. Journal of Healthcare Communications.

* cited by examiner

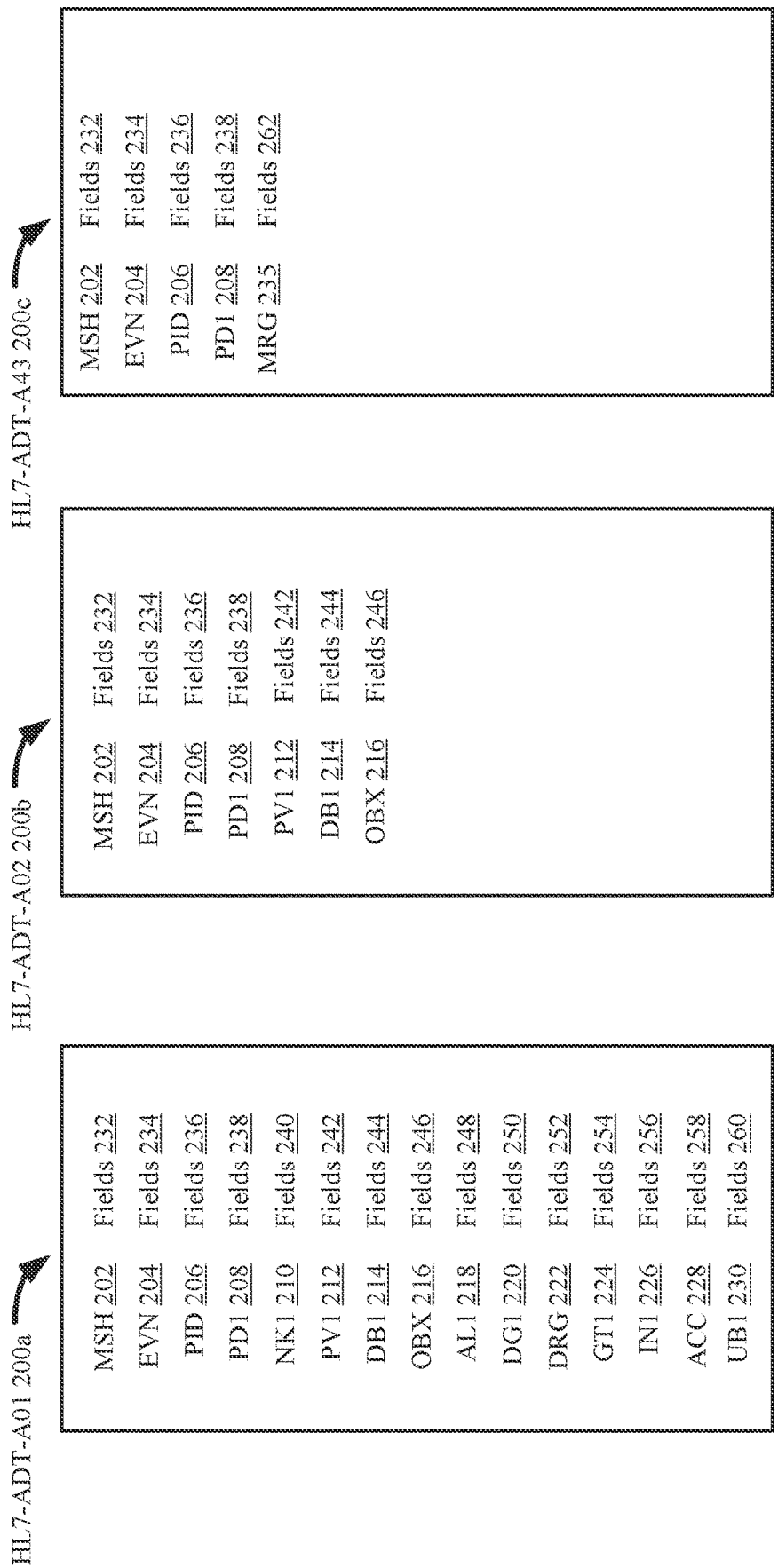

Figure 4D

202a → MSH|^~\&|AccMgr|1||20050110045504||ADT^A01|599102|P|2.3|||

204a → EVN|A01|20050110045502||||

206a → PID|1||10006579^^^1^MRN^1||DOE^JOHN^D||19241010|M|||1111 DEER ST^^BUCK^CA^99999000^^M|1|8885551212|8885552222|12|2|400077716^^^AccMgr^VN^1|123121234|||||||NO|

210a → NK1|1|DOE^BOB|SO|3583 DEER RD^^BUCK^CA^99999000|8885552222||Y|||||||||||

212a → PV1|1|||PREOP^101^1^1^^^S|3||37^DOE^WALT^^^^^^AccMgr^^^^C|||01||||1||37^DOE^WALT^^^^^^AccMgr^VN|4|||||||||1|G||20050110045253|||||

224a → GT1|1|8291|DOE^JOHN^D||111^DEER ST^^BUCK^CA^99999000|8885551212| 19241010|M| I|123121234|||1|#DEERSRUS Inc|111^DEER ST^^BUCK^CA^99999000|8885551212||PT|

220a → DG1|1|I9|71596^OSTEOARTHROS NOS-L/LEG ^19|OSTEOARTHROS NOS-L/LEG ||A|

226a → IN1|1|MEDICARE|3|MEDICARE|||||DEERSRUS Inc|19891001||4|DOE^JOHN^D|1|19241010|111^DEER ST^^BUCK^CA^99999000|||||||123121234A|||||PT|M|111 DEER ST^^BUCK^CA^99999000||||8291|

226b → IN2|1||123121234|DEERSRUS Inc|||123121234A||||||||||8885551212|

HL7-ORM-001 200d

| | |
|---|---|
| MSH 202 | Fields 232 |
| NTE 264 | Fields 276 |
| PID 206 | Fields 236 |
| NTE-1 266 | Fields 278 |
| PV1 208 | Fields 238 |
| IN1 226 | Fields 256 |
| AL1 218 | Fields 248 |
| ORC 268 | Fields 280 |
| OBR 270 | Fields 282 |
| DG1 220 | Fields 250 |
| OBX 216 | Fields 246 |
| CTI 272 | Fields 284 |
| BLG 274 | Fields 286 |

*Figure 5A*

Mapping Example
600

| Position 605 | HCS Format 607 | Healthcare Information Source 609 |
|---|---|---|
| 0 | PID 602a | PID 602b |
| 1 | Patient ID 604a | External ID 606b |
| 2 | External ID 606a | Patient ID 604b |
| 3 | Internal ID 608a | Internal ID 608b |
| 4 | Alternate Patient ID 610a | (Not Classified) |
| 5 | Patient Name 612a | Patient Name 612b |
| 6 | Mother's Maiden Name 614a | (Not Classified) |
| 7 | Date of Birth 616a | Date of Birth 616b |
| 8 | Sex 618a | Sex 618b |
| 9 | Patient Alias 620a | (Not Classified) |
| 10 | Race 622a | Race 622b |
| 11 | Address 624a | Address 624b |
| 12 | Country Code 626a | (Not Classified) |
| 13 | Phone number 628a | Phone number 628b |
| 14 | Phone number 630a | Phone number 630b |
| 15 | Primary Language 632a | Primary Language 632b |
| 16 | Marital Status 634a | Religion 634b |
| 17 | Religion 635a | Marital Status 635b |
| 18 | Patient Account Number 636a | (Not Classified) |
| 19 | SSN 638a | SSN 638b |
| 20 | Drivers License Number 640a | (Not Classified) |
| 21 | Mothers Identifier 642a | (Not Classified) |
| 22 | Ethnic Group 644a | Ethnic Group 644b |
| 23 | Birth Place 646a | (Not Classified) |
| 24 | Multiple Birth Indicator 648a | (Not Classified) |
| 25 | Birth Order 650a | (Not Classified) |
| 26 | Citizenship 652a | (Not Classified) |
| 27 | Veterans Military Status 654a | (Not Classified) |
| 28 | Nationality 656a | (Not Classified) |
| 29 | Patient Death Date and Time 658a | (Not Classified) |
| 30 | Patient Death Indicator 660a | (Not Classified) |

*Figure 6*

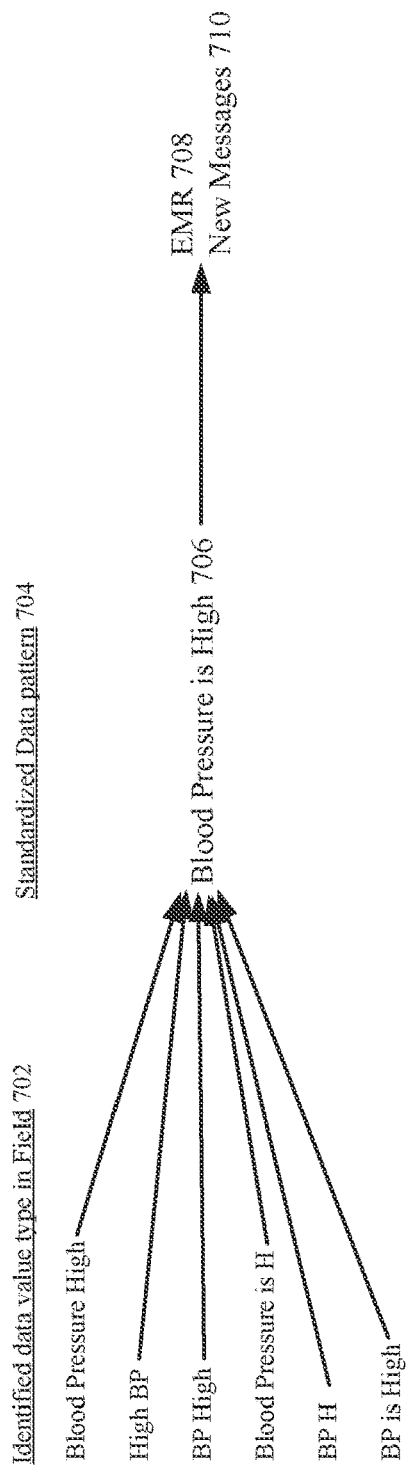

SYSTEMS AND METHODS FOR INTEGRATING COMMUNICATIONS IN A HEALTHCARE NETWORK

CROSS-REFERENCE TO RELATED APPLICATION

This application is a continuation of U.S. patent application Ser. No. 16/107,613 entitled: "SYSTEMS AND METHODS FOR INTEGRATING COMMUNICATIONS IN A HEALTHCARE NETWORK" filed on Aug. 21, 2018, which is incorporated herein by reference in its entirety for all purposes.

FIELD OF THE INVENTION

This invention generally relates to delivering healthcare services and more particularly, to communication interfaces in a healthcare network.

BACKGROUND

Electronic healthcare information networks link hospitals, insurers, laboratories and physician practices to provide healthcare services, such as services related to accessing healthcare information for patients, ordering labs for patients and billing patients. Some standards of communications are available that enable communications between healthcare providers in an electronic healthcare information network. For example, Health Level-7 (HL7) is a set of international standards used to transfer clinical and administrative data between software applications used by various healthcare providers.

Unfortunately, there are many different versions of HL7. In addition, many healthcare providers have customized versions of HL7. Thus, when integrating disparate healthcare providers into a common electronic healthcare information network, even when the healthcare providers utilize a common communication standard, such as HL7, a large amount of time is spent to ensure all the communications are being properly interpreted by all the participants in the network. Precision in the communications is essential because an improper transfer of patient's healthcare information can cause harm to the patients. In view of the above, method and apparatus are desirable that simplify the communication integration of healthcare providers into an electronic healthcare information network.

SUMMARY

Electronic healthcare systems are described. The electronic healthcare systems can include modules for accessing patient electronic medical records and ordering medical services. The electronic healthcare system (EHS) can include one or more communication interfaces configured to communicate with electronic devices. The electronic devices, such as mobile devices and servers can be associated with medical testing services, medical practices, health insurance providers and patients. In one embodiment, the EHS can be instantiated in a cloud computing environment including servers with processors, memory and communication interfaces.

In one embodiment, a portion of the communication interfaces in the EHS can be configured to implement health level 7 (HL7) communication messages. HL7 is an international standard which specifies a number of flexible standards, guidelines, and methodologies by which various healthcare systems can communicate with each other. Such guidelines or data standards are a set of rules that can allow information from healthcare applications to be shared and processed in a uniform and consistent manner. These data standards are meant to allow healthcare organizations to easily share clinical information.

Unfortunately, there are many different version of HL7 that have evolved over the years. In addition, many healthcare organizations customize HL7 in non-standard ways. Thus, when integrating HL7 communications from different health care organizations, custom interfaces can be required which translate HL7 communications in a first format associated with a first healthcare organization to a second format associated with a second healthcare organization.

Accurate translation of the communications is necessary because inaccurate communications can result in the loss of critical patient information and can possibly result in the implementation of improper medical procedures. Thus, the development of the custom interfaces for accurate communication translations can take months to implement. In view of the above, methods and apparatus are described as follows which can simplify and speed up the process of developing custom communication interfaces used to translate HL7 messages in an electronic healthcare system.

One aspect of the present disclosure can be related to a method in an electronic healthcare system including a plurality of health care information sources. The method can be generally characterized as including: 1) receiving a first plurality of HL7 messages from a first healthcare information source where each of the first plurality of HL7 messages includes a plurality of HL7 message segments; 2) parsing the first plurality of HL7 messages to identify a patient identification (PID) message segment among the HL7 message segments where the PID message segment includes a plurality of data types each associated with a data field in the PID message segment and where an order of the plurality of data types in the PID message segment from the first healthcare information source is unknown; 3) for each of the data fields in the PID message segment in each of the first plurality of HL7 messages, i) determining whether a data value is present; ii) when the data value is present, using the data value to determine a plurality of values of data features wherein the data features characterize the data value and where the plurality of values of the data features are used by a trained machine learning algorithm to classify the data value as one of the plurality of data types and iii) based upon the plurality of values of the data features, classifying using the trained machine learning algorithm the data value as one of the plurality of data types in the PID message segment where the trained machine learning algorithm is used to determine how to correctly parse the HL7 messages from the first healthcare information source; 4) for a first data field in the PID message segment in the first plurality of messages from the first healthcare information source, i) determining the first data field is classified as one of the plurality of data types a first number of times where the first number of times exceeds a first threshold value, ii) determining the first data field is classified as a first data type among the plurality of data types a percentage of the first number of times wherein the percentage exceeds a second threshold value and iii) determining a first position of the first data field in the PID message segment; 5) receiving a second plurality of HL7 messages from the first information source including the PID message segment; and 6) parsing the PID message segment in the second plurality of HL7 messages using the first position of the first data field determined using the trained machine learning algorithm to determine first data values of the first data field associated with the first data type.

In particular embodiments, the trained machine learning algorithm can be selected from among the group consisting of a neural net, a decision tree, a naive Bayes classifier, ordinary least squares regression, a logistic regression, a support vector machine, an ensemble method, a clustering algorithm, a principal component, a singular value decomposition and an independent component analysis. The data features can be selected from the group consisting of a total number of letters in the data value, a total number of numbers in the data value, a ratio between the total number of letters to the total number of numbers in the data value, a total number of characters in the data value, a total number of sub-fields in each data field, a position number in the data fields of the PID message segment, an N-gram, a cosine similarity, a Jaccard similarity, a Levenshtein distance and a feature hashing.

In other embodiments, the first threshold value can be greater than one hundred. In another embodiment, the first threshold value can be between about one hundred and two hundred. The second threshold value can be greater than ninety percent. In a further embodiment, the threshold value can be between about seventy five and ninety five percent.

In yet other embodiments, the plurality of data types can be selected from a first group consisting of a patient ID, an External ID, a patient name, a date of birth, a sex, an address, a phone number, a primary language, a marital status and a social security number. In addition, the plurality of data types can be selected from a second group consisting of an alternate patient ID, a mother's maiden name, a race, a country code, a religion, a driver's license number, a birth place, multiple birth indicators, a citizenship, a veteran's military status, a nationality, a patient death data and time and a patient death indicator.

In yet further embodiments, the method can further comprise: 1) generating a HL7 message for a second healthcare information source wherein the HL7 message includes the PID message segment and wherein the first data field associated with the first data type in the PID message segment is in a second position different from the first position, 2) updating electronic medical records in a healthcare information database using the first data values from the first data field associated with the first data type parsed from the second plurality of HL7 messages, 3) prior to parsing the PID message segment in the second plurality of HL7 messages, outputting the first position of the first data field and the first data type determined using the trained machine learning algorithm, outputting example values associated with the first data field and receiving an input indicating the first data type is correct and 4) training the machine learning algorithm to classify the plurality of data types in the PID message segment using the data features. The data features can be weighted during the training of the machine learning algorithm.

In another embodiment, the method can further comprise: 1) for a second data field in the PID message segment in the first plurality of messages from the first healthcare information source, i) determining the second data field is classified as one of the plurality of data types the first number of times where the first number of times exceeds a third threshold value, ii) determining the second data field is classified as a second data type among the plurality of data types the percentage of the first number of times where the percentage exceeds a fourth threshold value and iii) determining a second position of the second data field in the PID message segment; and 3) parsing the PID message segment in the second plurality of HL7 messages using the second position of the second data field determined using the machine learning algorithm to determine second values of the second data field associated with the first data type. In the above embodiment, the third threshold value can be equal to the first threshold. Further, the fourth threshold can be equal to the second threshold.

In a yet further embodiment, the method can further comprise: 1) receiving a third plurality of HL7 messages from a second healthcare information source where each of the third plurality of HL7 messages includes the plurality of HL7 message segments; 2) parsing the third plurality of HL7 messages to identify the patient identification (PID) message segment among the HL7 message segments where a second order of the plurality of data types in the PID message segment from the second healthcare information source is unknown; 3) for each of the data fields in the PID message segment in each of the third plurality of HL7 messages, i) determining whether the data value is present; ii) when the data value is present, using the data value to determine the plurality of values of data features where the data features characterize the data value and iii) based upon the plurality of values of the data features, classifying using the trained machine learning algorithm the data value as one of the plurality of data types in the PID message segment; 4) classifying, using the trained machine learning algorithm, a second data field in a second position of the PID message segment in the third plurality of messages from the second healthcare information source as the first data type. In the above embodiment, the first position and the second position can be in a different position in the PID message segment for the first healthcare information source as compared to the second healthcare information source.

In yet another embodiment, the method can further include 1) parsing the first plurality of HL7 messages to identify a second message segment among the HL7 message segments where the second message segment includes a second plurality of data types each associated with one of the data fields in the second message segment and where an order of the second plurality of data types in the second message segment from the first healthcare information source is unknown; 2) for each of the data fields in the second message segment in each of the first plurality of HL7 messages, i) determining whether the data value is present; ii) when the data value is present, using the data value to determine a plurality of values of second data features wherein the plurality of values of the second data features are used by the trained machine learning algorithm to classify the data value as one of the second plurality of data types and iii) based upon the plurality of values of the second data features, classifying using the trained machine learning algorithm the data value as one of the second plurality of data types in the second message segment.

Another aspect of the disclosure can be related to a method in an electronic healthcare system including a plurality of health care information sources. The method can be generally characterized as comprising: 1) receiving a first plurality of HL7 messages from a first healthcare information source where each of the first plurality of HL7 messages includes a plurality of HL7 message segments; 2) parsing the first plurality of HL7 messages to identify a first message segment among the HL7 message segments where the first message segment includes a plurality of data types each associated with a data field in the first message segment and where an order of the plurality of data types in the first message segment from the first healthcare information source is unknown; 3) for each of the data fields in the first message segment in each of the first plurality of HL7 messages, i) determining whether a data value is present; ii) when the data value is present, using the data value to determine a plurality of values of data features wherein the data features characterize the data value and wherein the plurality of values of the data features are used by a trained machine learning algorithm to classify the data value as one of the plurality of data types and iii) based upon the plurality of values of the data features, classifying using the trained machine learning algorithm the data value as one of the plurality of data types in the first message segment wherein the trained machine learning algorithm is used to determine how to correctly parse the HL7 messages from first information source; 4) for a first data field in a first position of the first message segment in the first plurality of messages from the first healthcare information source, determining the first data field is classified as a first data type; 5) receiving a second plurality of HL7 messages from the first information source including the first message segment; and 6) parsing the first message segment in the second plurality of HL7 messages using the first position of the first data field determined using the trained machine learning algorithm to determine first values of the first data field associated with the first data type. In particular embodiments, the first message segment can only be present in a portion of the first plurality of HL7 messages. In addition, the first message segment can be a patient identification message segment.

BRIEF DESCRIPTION OF THE DRAWINGS

The included drawings are for illustrative purposes and serve only to provide examples of possible structures and process steps for the disclosed inventive systems and methods for healthcare services. These drawings in no way limit any changes in form and detail that may be made to the invention by one skilled in the art without departing from the spirit and scope of the invention.

FIG. 4A is a diagram of a HL7-ADT-A01 message in accordance with the described embodiments.

FIG. 4B is a diagram of a HL7-ADT-A02 message in accordance with the described embodiments.

FIG. 4C is a diagram of a HL7-ADT-A43 message in accordance with the described embodiments.

FIG. 4D is an example of a HL7-ADT-A01 message in accordance with the described embodiments.

FIG. 5A is a diagram of a HL7 ORM event message in accordance with the described embodiments.

FIG. 6 illustrates an example of a mapping of HL7 messages using machine learning algorithm to generate a message translator from a healthcare information source in a healthcare network in accordance with the described embodiments.

FIG. 7 illustrates an example of transforming a data value from a data field within a message segment from HL7 messages using a trained machine learning algorithm in accordance with the described embodiments.

DESCRIPTION OF THE PREFERRED EMBODIMENTS

Figure 1:
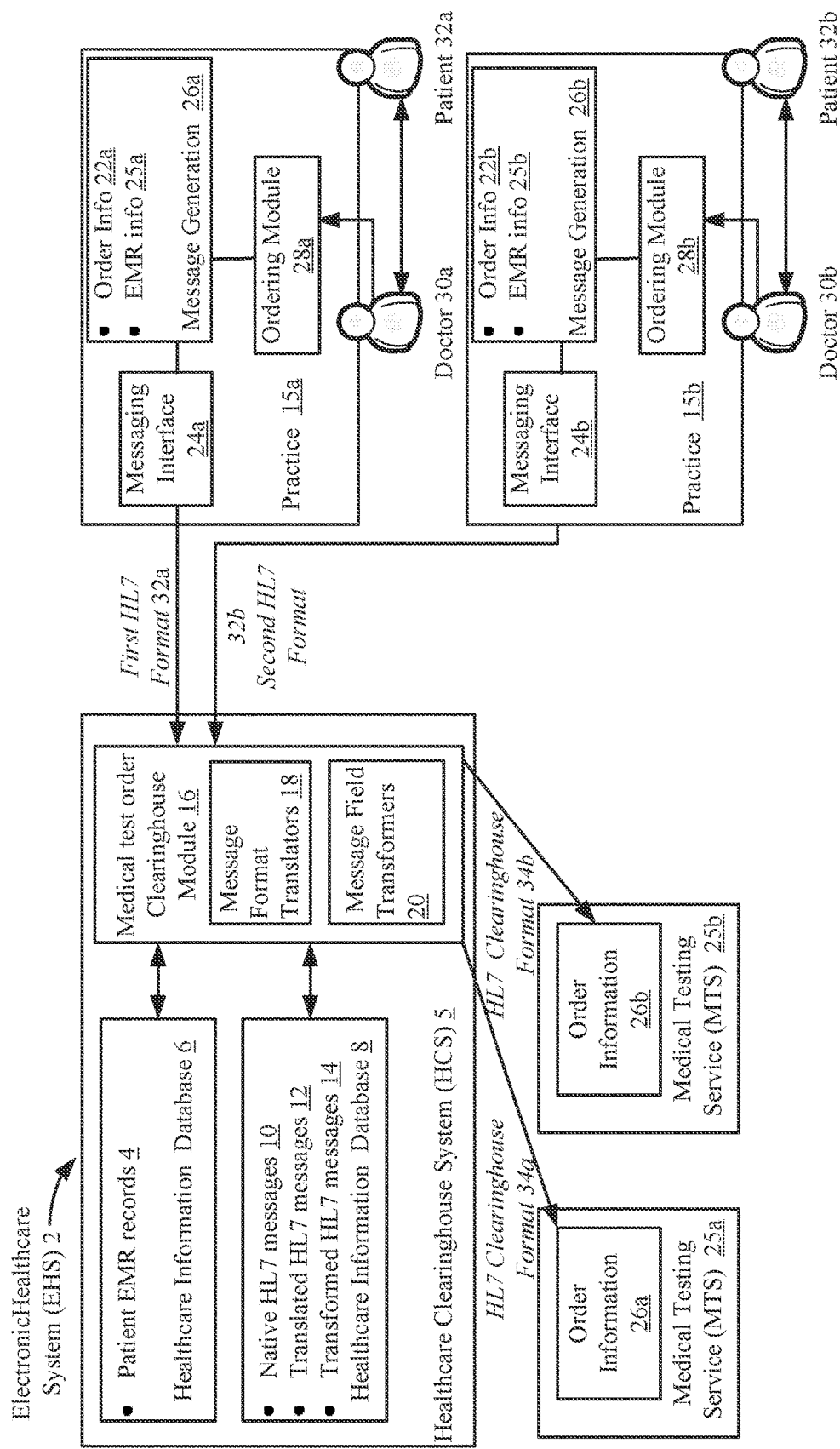
FIG. 1 is a block diagram of a system for delivering healthcare services in accordance with the described embodiments.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details.

An Electronic healthcare system (EHS) is described in more detail below. The EHS can include modules for accessing patient electronic medical records and ordering medical services. In various embodiments, the EHS can be instantiated in a cloud based computing environment. One or more custom communication interfaces can allow software applications within the EHS to communicate with one another via messaging formats, such as HL7.

In one embodiment, a healthcare clearinghouse system (HCS) can be provided. The HCS can be configured to maintain healthcare information databases including patient electronic medical records (EMRs) for a plurality of healthcare entities. Further, the HCS can be configured to receive medical test orders from medical practices, update patient electronic medical records based upon the test orders and communicate information regarding the medical test orders to medical testing services, such as laboratories.

The HCS can communicate with a plurality of healthcare entities using an HL7 communications. HL7 stands for Health Level-7. HL7 can refer to a set of standards for transfer of clinical and administrative data between software applications by various healthcare providers. Some details of the HL7 communication architecture are described below. Additional details of the HL7 communication architecture can be found at www.hl7.org (Health Level Seven International, 3300 Washtenaw Ave, Suite 227, Ann Arbor, Mich.).

In some instances, the HL7 communications can utilize custom interfaces that are used to parse the HL7 communications from some of the healthcare entities. The custom communication interfaces can account for different versions of the HL7 communications used by the different entities. In addition, the custom communication interfaces can account for non-standard implementations which are sometimes utilized.

In the past, the development of custom interfaces has taken months. The custom interface development process can include thoroughly reviewing all the different types of HL7 messages and formats from a particular healthcare information source and verifying the correct parsing of actual messages that are received at the HCS. As will be described in more detail as follows, machine learning can be applied to speed up the custom interface generation process.

In particular, machine learning algorithms can be trained and then applied to classify data types parsed from HL7 messages from the particular healthcare information source. The classified data types can be used to develop a custom mapping that describes the format of the HL7 messages from the particular healthcare information source. The custom mapping can be implemented in a custom communication interface at the HCS associated with the particular healthcare information source. Data parsed from HL7 messages using the custom mapping can be used to update patient electronic medical records maintained at the HCS.

In more detail, with respect to FIG. 1, a block diagram of a system for delivering healthcare services is discussed. With respect to FIG. 2, a block diagram illustrating HL7 message delivery and machine learning algorithm training is described. With respect to FIG. 3A, a method of classifying information in an HL7 message is discussed. With respect to FIG. 3B, a method of recognizing data patterns and transforming information in an HL7 message is described. With respect to FIGS. 4A to 5B, different types of HL7 messages including admit, discharge and transfer (ADT) messages and order response messages (ORM) are discussed. FIG. 6 illustrates an example of a mapping of HL7 messages using a machine learning algorithm to generate a message translator from a message source in a healthcare network. FIG. 7 illustrates an example of transforming field data from HL7 messages using a machine learning algorithm.

FIG. 1 is a block diagram of a system 2 for delivering healthcare services. The system 2 can include a plurality of medical testing services (MTS), such as MTS 25a and MTS 25b, a plurality of medical practices, such as medical practice 15a and medical practice 15b. In addition, can include a plurality of insurance providers (not shown).

The MTS and the medical practices can utilize applications which communicate with the healthcare clearinghouse system (HCS) 5. The applications at the MTS and the medical practices can be referred to as healthcare information sources. In particular embodiments, the HCS 5 can communicate with the healthcare information sources using HL7 formatted communications. In other embodiments, other communication standards can be used such as a "X12-270/271" message protocol. The "X12-270/271" message protocol is often used to communicate with insurance providers. Details of the "X12-270/271" message protocol are described in more detail in co-pending U.S. application Ser. No. 15/896,514, filed Feb. 14, 2018, by Bess et al., titled "SYSTEMS AND METHODS FOR HEALTHCARE FEES TRANSPARENCY AND COLLECTIONS AT THE TIME OF SERVICE," which is incorporated by reference in its entirety and for all purposes.

A patient, such as 32a or 32b, can visit a medical practice, such as practices 15a or 15b, for a visit with a doctor, such as 30a or 30b. During or prior to the visit, the doctor, such as 30a or 30b, can utilize an electronic device which allows healthcare information about the patient to be accessed, such as an electronic medical record (EMR) system. In one embodiment, the EMR for the patients 32a and 32b can be managed at the HCS 5. For example, the healthcare information database 6 can include EMRs for patient 32a and 32b. In other embodiment, the practices 15a or 15b may include or may have access to a separate EMR system which is configured to communicate with HCS 5.

In one embodiment, via the electronic device used by the doctor, such as 30a or 30b, the message generation modules, such as 26a or 26b, can be used to generate a message, such as 25a or 25b, to contact the HCS 5 and retrieve an EMR for patient. The generated messages can be sent via the message interfaces, such as 24a and 24b, which can allow the HCS 5 to be contacted over a network. As described above, the HCS 5 can include an EMR system. This transaction can be an HL7 (Health Level 7) compliant communication.

In some instances, the HCS can be instantiated in the cloud and include processors, memory including volatile and non-volatile memory, and network communication interfaces. Additional details of an EMR system including a master patient index that can be utilized with the HCS 5 are described in co-pending U.S. patent application Ser. No. 15/605,826, filed May 25, 2017 and titled "Systems and Methods for Managing a Master Patient Index including Duplicate Record Detection," which is incorporated herein by reference in its entirety and for all purposes.

As described above, in particular embodiments, information can be communicated using an HL7 message format. In one embodiment, practice 15a can communicate using a first HL7 message format 35a and practice 15b can communicate using a second HL7 message format 35b. The HL7 message format is described in more detail with respect to FIGS. 4A-5B. The HL7 message communication is provided for the purposes of illustration only is not meant to be limiting.

The first HL7 format 35a can be different from the second HL7 format 35b. In one example, the formats, 35a and 35b, can be different because the practices 15a and 15b utilize different HL7 versions. In another example, the practice 15a or 15b, the formats can be different because the practices 15a or 15b have implemented a non-standard, customized version of HL7.

The medical test order clearinghouse module 16 can be configured to receive HL7 communications from different healthcare information sources, identify the healthcare information source and apply a custom HL7 message format translator that is associated with the healthcare information source. For example, the module 16 can store a first custom HL7 message format translator associated with practice 15a and a second custom HL7 message format translator associated with practice 15b in a memory device. In general, the HCS 5 can store a plurality of message format translators 18.

When a HL7 message is detected from the practice 15a, which is in a first HL7 format 35a, the HCS 5 can use the first custom message translator stored in message format translators 18 to correctly interpret the HL7 message from the messaging interface 24a in the first HL7 format 35a. Similarly, when a HL7 message is detected from the practice 15b, which is in a first HL7 format 35b, the HCS 5 can use the second custom message translator stored in message format translators 18 to correctly interpret the HL7 message from the messaging interface 24b in the second HL7 format 35b. The correct interpretation of the messages, which is described in more detail below, can involve parsing the fields and the subfields of the HL7 messages and then matching the data values in the fields and the subfields to a data type associated with the field of the subfield.

As an example of parsing and matching data values in the fields and sub fields, a data value can be parsed from a first message segment in a first HL7 message. The position of the data value in the first message segment can be determined. For example, a message segment associated with patient demographic data can have thirty fields total and the data value can be determined to be in the $10^{th}$ data field. Based on the identity of the message segment and its position in the message segment, the first message translator can indicate that the data value is associated with an address. An HL7 message can have plurality of message segments and the number of data fields can vary from message segment to message segment. Further, the different HL7 messages can have different combinations of message segments.

As will be described in more detail below, initially when a health information source is brought onboard and coupled to the HCS 5, a custom translator may not be available for the health information source. Thus, when an HL7 message is received, the data fields in the message segments can be parsed for data values. However, data types associated with each of the data fields can be unknown. For example, it can be unknown whether a data value in a data field of a message segment is a name, a phone number or a date of birth.

As will be described in more detail below, a trained machine learning algorithm can be used to classify a data value as one of the data types associated with a message segment. For example, a first data value in a first data field in a determined position of a message segment, which is a name can, be classified as a name by a machine learning algorithm. As another example, a second data value in a second data field in a determined position of a message segment, which is an address, can be classified as an address, by a machine learning algorithm.

When the machine learning algorithm is able to classify the data values as particular data types from a particular type of message segment in a number of HL7 messages, a mapping of the data types in the particular message segment can be determined. For example, the mapping can specify, a first data type is in a first position of the message segment, a second data type is in a second position of the message segment, a third data type is in a third position of the message segment, etc. The mapping can provide a basis for generating a custom HL7 message translator for the healthcare information source. The custom HL7 message translator can be stored in the message format translators 18. Additional details of using a machine learning algorithm to generate a custom HL7 message translator are described with respect to FIGS. 2 and 3A.

Returning to FIG. 1, in another embodiment, the EMR for patient 32a can be stored locally on a device at the practice the 15a. Thus, the electronic device utilized by the doctor 30a can be configured to retrieve information associated with an EMR for patient 32a from a local device associated with the practice. Similarly, the EMR for patient 32b can be stored locally on a device at the practice the 15b.

In a further embodiment, the EMRs can be stored on a remote device which provides an EMR system accessible to the practice, such as 15a or 15b. The EMR system can be separate from the EMR system associated with HCS 5. Information from the patient's EMR retrieved from the EMR system can be output to the doctor's electronic device.

In one embodiment, the doctor's electronic device can be configured to execute an ordering module, such as 28a or 28b. The ordering module can allow the doctors, such as 30a or 30b, to access the patient's EMR, such as patient 32a or 32b. The ordering modules, 28a or 28b, can also be configured to generate an interface that allows the doctors, such as 30a or 30b, to order one or more medical tests for patient, 32a or 32b. The medical test order generated by the ordering module can specify a medical testing service, such as 25a or 25b, which is to fulfill the medical test which has been ordered.

For example, doctor 30a can order blood tests for the patient 32a via an electronic device. After the blood tests are ordered, the patient 32a can proceed to a phlebotomy area where blood or other specimen is collected. The phlebotomist draws the blood from the patient and places the blood in the appropriate test tubes.

The phlebotomist can also print a copy of the order, which is also called a lab requisition. In some cases, the requisition also contains "crack and peel" labels, where patient's name and bar codes are printed. These labels are placed on the test tubes.

Next, the phlebotomist can place the printed requisition into a plastic bag together with the tubes filled with blood. Each test tube can be labeled with patient's name and bar code. The bag can later be picked up by a currier and brought to the laboratory. The laboratory can be example of an MTS, such as 25a or 25b. Meanwhile, the laboratory can have received the electronic version of the requisition and can simply match them up with the specimen when it arrives.

After the order including one or more medical tests is entered via the ordering module 28a, information about the order can be sent to the HCS 5 via an HL7 message. For example, message generation 26a can be used to generate the HL7 message. Then, the HL7 message with the order can be sent to the HCS 5 via the messaging interface 24a.

The module 16 can receive the HL7 message from practice 15a in a first HL7 format 32a. Then, a first message format translator can be applied to the message to correctly interpret the data fields in the HL7 message. In some instances, information contained in the HL7 message can be used to update an EMR of a patient associated with the HL7 message. The updated EMR can be stored in the database 6.

In particular embodiments, a message field transformer in message field transformers 20 can be applied to data values associated with one or more data fields in the HL7 message. The message field transformer may recognize a data value in a data field, such as a description of a patient condition associated with a test order and convert it to a standard format. For example, a description of a patients temperature can be written in different formats, such as "temperature is high," "temp is high," "temp is h," "temperature is above normal," etc.

A first transformer in the message field transformers can recognize that a temperature condition is being described and then convert it to a standard format. For example, occurrences of a description about the temperature being high can be recognized using a trained machine learning algorithm and then each transformed into a common format, such as "temperature is above normal." For example, an occurrence of any of the descriptions, "temperature is high," "temp is high," "temp is h," "temperature is h," can be recognized and transformed to the description "temperature is above normal."

In particular embodiments, one or more of i) HL7 messages in a native format 10, ii) HL7 messages in a translated format 12 and iii) HL7 messages with transformed data values 14 can be stored to healthcare information database 8. For example, an HL7 message from practice 15a can be stored to database 8 in the first HL7 format 32a and a message from practice 15b can be stored to database 8 in the second HL7 format 32b. Alternatively or in addition, the HL7 message from practice 15a can be translated from the first HL7 format 32a to a third HL7 format and the HL7 message from practice 15b can be translated from the second HL7 format 32b to the third HL7 format.

The third HL7 format can be a HL7 format associated with the HCS 5 in which all HL7 messages are translated. The HL7 messages in the third HL7 format can be stored as translated HL7 messages 12 to database 8. In addition, any HL7 messages with transformed data values can be stored as transformed HL7 messages 14.

After the messages with test order information are received and processed via the message format translators 18 and/or the message field transformers 20, the HCS 5 can generate and send an HL7 message with the test order information to the medical testing services, such as 25a and 25b. In one embodiment, the HL7 messages to MTS 25a or 25b can be in a HL7 clearinghouse format, such as the third HL7 format described in the previous paragraph. In another embodiment, the HCS 5 can use a mapping associated with a message format translator that is particular to MTS 25a or MTS 25b. Using the message format translators, HL7 messages can be generated that are compatible with an HL7 message format used by MTS 25*a* and MTS 25*b*.

Figure 2:
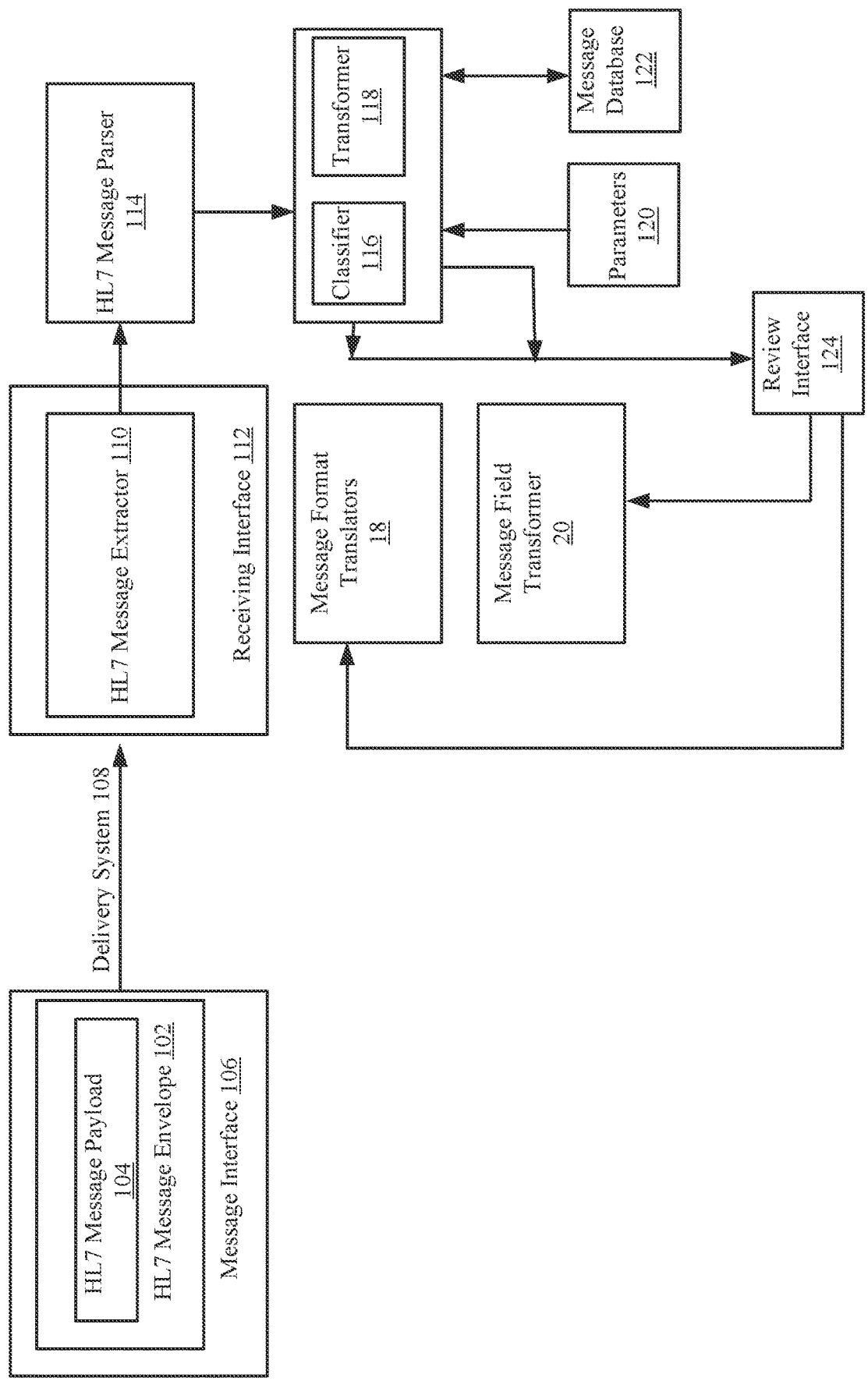
FIG. 2 is a block diagram illustrating HL7 message delivery and machine learning algorithm training in accordance with the described embodiments.

Next, with respect to FIG. 2, the construction HL7 messages, the parsing of HL7 messages, the application of machine learning algorithms to develop a HL7 message format translator and the application of machine learning algorithms to transform messages is described. FIG. 2 includes a block diagram illustrating HL7 message delivery. The HL7 message delivery includes electronic communication between various electronic devices via a delivery system, such as the Internet.

Figure 5B:
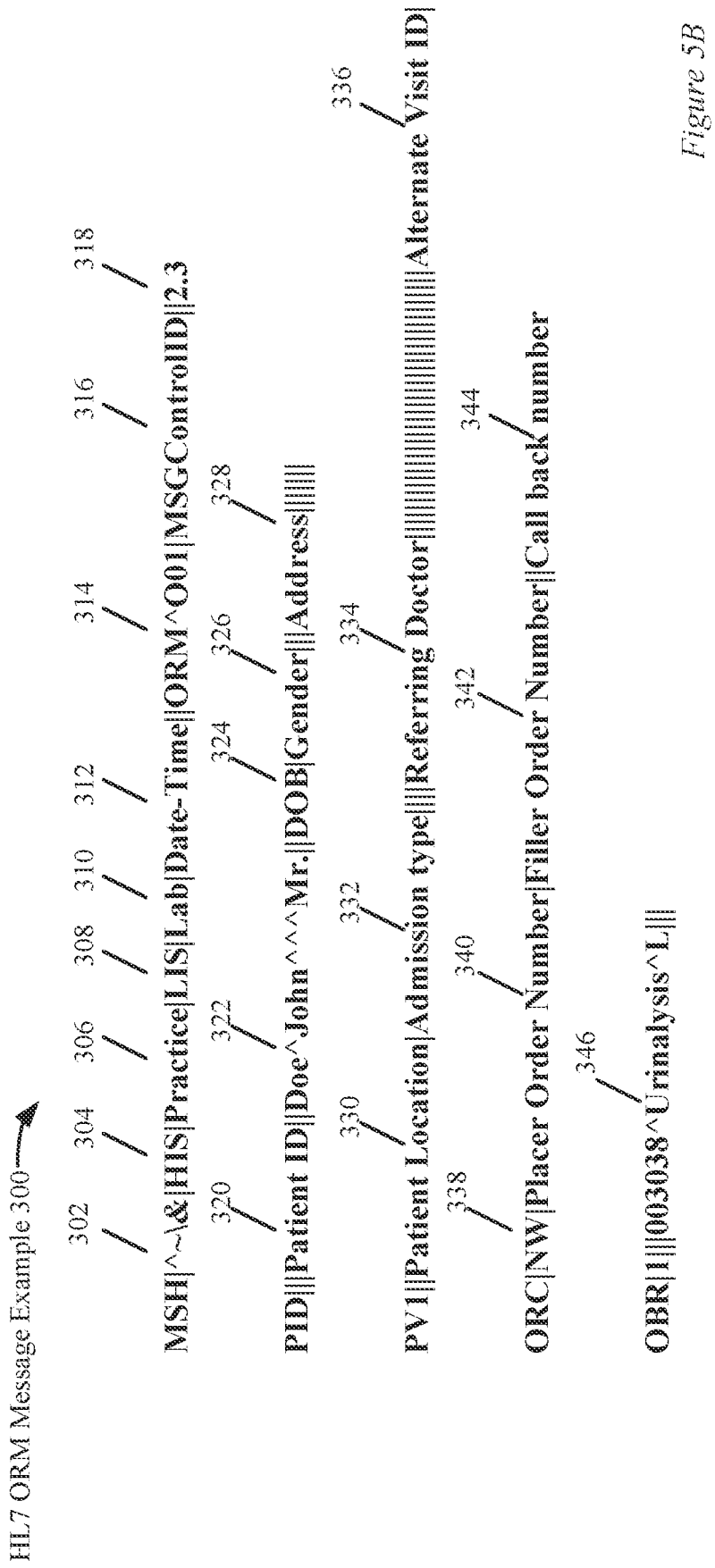
FIG. 5B is an example of a HL7 ORM event message in accordance with the described embodiments.

In FIG. 2, an application (not shown) can be used to generate an HL7 message payload. For example, in FIG. 1, based upon a received order in ordering module 28*a*, the message generation module 26*a* can be configured to construct an HL7 message payload 104 which is sent to an HCS 5. FIGS. 4D and 5B show examples of HL7 message payloads for a HL7 ADT message and a HL7 ORM message, respectively.

The message interface 106 (see also, 24*a* and 24*b* in FIG. 1) can construct an HL7 message envelope 102. For example, the message interface 106 can be configured to embed the message payload 104 in an email with specific attributes and the send the email via the delivery system 108, such as the Internet, SFTP or HTTPS. The HL7 message can be directed to a receiving interface 112. When the HCS 5 is a recipient of the HL7, then the receiving interface 112 can be located in the HCS 5.

The receiving interface 112 can be configured to extract the message payload, using the HL7 message extractor 110, from HL7 Message envelope 102. Then, the HL7 message parser 114 can be configured to extract information, such as data values in data fields, from the HL7 message payload 104. The parsing can include recognizing message segments in the HL7 message, extracting data values from data fields in each message segment and then applying a message format translator that maps a position of the data field to a known data type associated with the message segment. For example, the message segment can be identified as a patient identification (PID) message segment and the fifth position in the data fields of the PID message segment can be associated with a patient's name (e.g., see FIG. 6).

In some instances, a message translator may not be available for a particular information source. For example, when a new medical practice is first coupled to the HCS 5, a message format translator may not be available for the medical practice. To develop the message format translator, one or more trained machine learning algorithms can be applied to the data values in one or more of the message segments associated with the received HL7 message to classify the data values as data types associated with each message segment. This process can be repeated over a plurality of HL7 messages to generate confidence that the data values associated with a particular position in a message segment are correctly classified. The mapping between positions in the message segment and the classified data types can provide a mapping that can be used as a message format translator.

In this example, the message parser 114 may receive an HL7 message from a first healthcare information source and parse the HL7 message for message segments. Then, for one or more of the message segments, the HL7 message parser can determine data values in data fields associated with the one or more message segments. Initially, the data values in each position of the data fields can be assumed to be of unknown data type.

In each message segment, only a portion of the data fields can have data values. For example, in a first message segment of a first HL7 message a data value can be present in a first, a second, a third, a fifth and a seventh position of the data fields of a message segment and not present in the fourth and sixth positions. The data fields which include data values can vary from message to message. For example, a first message segment in a second HL7 message can include data values in the first through seventh position.

Next, data features values can be determined for the data value in each field. A data feature value can characterize a data value or the data field from which the data value is obtained. The data feature values can be used by a trained machine learning algorithm to classify the data value as one a plurality of data types associated with the message segment from which the data value is extracted.

A first example of a data feature can be a number of characters associated with the data value. For example, "Jun. 26, 2001" can be associated with twelve characters. A second example of a data feature can be a number of words or units in the data value. For example, "Jun. 26, 2001 can be considered have three units. A third example of a data feature can be the number of letters which is four in this example. A fourth example of a data feature can be a number of numbers in the data value, which has a value of six in this example. A fifth example of data feature can be a ratio of the total number of numbers to the total number of characters or a total number of letters to a total number of characters, which have values of 6/12 and 6/12, respectively, in this example.

Yet another example of data feature can be lengths of the character strings. In "Jun. 26, 2001," the length of the character strings is four, three and four respectively. Also, the pattern of character strings, i.e., four, three and four can be used as a data feature.

In another example, the position in the data field of a message segment can be used as a data feature. For example, the data value can be associated with the fourth field of the message segment. In yet another example, a data value in a data field can be associated with a number of subfields. The subfields can denote a number of sub-values that a data field can include. The number of subfields can be determined for a data value in a data field and used as a data feature.

In another example, an N-gram can be determined for a data value. In the fields of computational linguistics and probability, an n-gram can be a contiguous sequence of n items determined from the data value. The items can be phonemes, syllables, letters, words or base pairs. The probability of combinations of n-grams occurring can be used to classify the data types.

Another example of a data feature can be Term Frequency-Inverse Document Frequency (TF-IDF). This technique assumes that, from a document corpus, a machine learning algorithm can get more information from the rarely occurring terms than frequently occurring terms. Using a weighted scheme, this technique can help to score the importance of terms. The terms occurring frequently can be weighted lower and the terms occurring rarely get weighted higher. TF can be calculated as: frequency of a term in a document/all the terms in the document. IDF can be calculated as: ratio of log (total documents in the corpus/number of documents with the 'term' in the corpus). Finally, TF-IDF can be calculated as: TF times IDF.

A further example of a data feature can be cosine similarity. This measure can help to find similar documents. It's one of the commonly used distance metric used in text analysis. For a given two vectors A and B of length n each, cosine similarity can be calculated as a dot product of two unit vectors.

Yet an additional example of a data similarity can be a Jaccard similarity. A Jaccard similarity can be another distance metric used in text analysis. For a given two vectors (A and B), it can be calculated as ratio of (terms which are available in both vectors/terms which are available in either of the vectors). It's formula is: (A∩B)/(A U B). To create features using distance metrics, first cluster of similar documents can be created and assigned a unique label to each document in a new column.

A further example of a data feature can be Levenshtein Distance. A Levenshtein distance can be used to create a new feature based on distance between two strings. It can find the shorter string in longer texts and returns the maximum value as one if both the shorter string is found. For example, calculating Levenshtein distance for string "Alps Street 41" and "1st Block, Alps Street 41" will result in one.

A final example of a data feature can be feature hashing. This technique can implement hashing which helps in reducing the dimension of document matrix (lesser columns). It doesn't use the actual data, instead it can use the indexes[ij] of the data, thus it processes data only when needed. Thus, it can take lesser memory in computation.

Returning to FIG. 2, after the data values from the data fields in a message segment in an HL7 message are extracted, the data values can be passed to the classifier 116. The classifier 116 can determine the data feature values associated with each data value. Then, the data feature values can be used as input to a trained machine learning algorithm used by the classifier 116.

The trained machine learning algorithm can be configured to classify the data values based on the data feature values determined for each data value in a data field. For example, the data value in a first data field can be "Jun. 26, 2001." The trained machine learning algorithm can determine data feature values using one or more of the data features described above. Then, based upon the data feature values, the trained machine learning algorithm may classify the data value as a date of birth.

The trained machine learning can be configured to classify the data value as one of the data types associated with a message segment from which the data value is obtained. For example, in FIG. 7, data types for a PID message segment are listed. The trained machine learning algorithm may or may not classify a data type correctly.

This process can be repeated for each of the data fields which have data values. Then, the classified HL7 message can be stored in the message database 122. The classified HL7 message can include classified data values associated with one or more different message segments in the message.

In some instances, the data feature values can be weighted. For example, the data feature values can be multiplied by some factor prior to being input into the trained machine learned algorithm. The weighting factors for each of the data features can be stored in the parameters database 120.

The classification of data values in data fields of message segments within the HL7 messages from a first information source can be repeated as new messages are received. After a data values in a data field of message segment have been classified a number of times, such as over a hundred times or between one hundred and two hundred times, the classifier 116 can determine whether the data field has been classified as a particular data type a percentage of the time which exceeds a second threshold value.

In general, the classifier 116 can be configured to determine whether a number of times data values in a data field have been classified and whether the number of times exceeds a first threshold value. The first threshold value can vary from data field to data field. The classifier 116 can be configured to determine a percentage of the times that the data values in a data field have been classified as particular data types and whether the percentage of one of the particular data types exceeds a second threshold value. The second threshold value can also vary from data field to data field. The first threshold values and the second threshold values can be stored in the parameters database 120.

For example, the classifier 116 can determine that a particular data field has been classified one hundred fifty times and that the one hundred fifty times exceeds a first threshold value of one hundred forty nine times. Further, the classifier 116 can determine that the particular data field has been classified as a first data type ninety two percent of the time. The ninety two percent of the time can exceed a second threshold value. For example, the particular data field may have been classified as a first data type, 92% percent of the time, as a second data type, 5% percent of the time and as a third data type, 3% of the time.

The process of determining whether a particular data field has been classified a number of times, which exceeds a first threshold value, and classified as a particular data type, which exceeds a second percentage threshold value, can be repeated for all or a portion of the data fields in a particular message segment. Only a portion of the data fields may be classified by the machine learning algorithm because a particular health information source may not populate one or more of the data fields or one or more of the data fields may be infrequently populated. When one of the data fields is not classified by the trained machine learning algorithm, then the classifier 116 may attempt to classify the data field based upon its position in the data field and based upon the remaining data types associated with the message segment which have not been classified using the trained machine learning algorithm.

Next, the portion of the data fields classified using the trained machine learning algorithm as well as the data fields classified based upon their position in the message segment and via a process of elimination as described in the previous paragraph can be verified. A review interface 124 can be provided which lists data types determined for each of the positions in the data fields for a first message segment. This information can be output to a display. In addition, the review interface 124 can provide examples of data values from the data fields which were obtained from the HL7 messages from a healthcare information source. The review interface 124 can output this information to a display.

Based upon the example data values and the classification of the data values determined from the trained machine learning algorithm, a user can confirm whether the data values have been correctly classified. The review interface 124 can be configured to receive the confirmation for each of the data fields in a message segment, which have been classified. When the classification of the data fields is confirmed, the classification of the data fields can be stored as a first message format translator for the first healthcare information source in the message format translators 18.

Next, a second plurality of HL7 messages can be received from the first healthcare information source. The second plurality of HL7 messages can be interpreted using the first message format translator stored in the message format translators 18. In addition, information parsed from the second plurality of HL7 messages using the first message format translator can be used to update patient EMRs.

The message transformer 118 can be configured to transform particular data values from a data field of a known data type in a first message segment from a first format to a second format. The trained machine learning algorithm, which can be different from the trained machine learning algorithm used to classify a data field as a particular data type, can be used to classify data values within the classified data field as particular types of data value. For example, a data field can be classified as clinical observations. Then, within the clinical observations, a particular data value type can be the observation that "temperature is high."

After the particular data value type is classified, the particular data value type can be transformed from a first format to a second format. For example, "temperature is high" can be transformed to "temperature is above normal." As another example, "temp is h" can be transformed to "temperature is above normal."

The classification of different data values as particular types of data values can again be confirmed via review interface 124. Then, after confirmation, the message field transformer for a healthcare information source can be stored to the message field transformers 20. The message field transformers 20 can be used to transform the data values in different data fields from a first format to a second format for different healthcare information sources. Further details of this process are described with respect to FIGS. 3B and 7.

In alternated embodiment, the messages described above can be translated from an first HL7 format to an FHIR (Fast Healthcare Interoperability Resources (FHIR) compatible format. FHIR is a standard describing data formats and elements (known as "resources") and an application programming interface (API) for exchanging electronic health records. The standard was created by the HL7 healthcare standards organization.

FHIR builds on previous data format standards from HL7, like HL7 version 2.x and HL7 version 3.x. But, it can be easier to implement because it uses a more recent web-based suite of API technology, including a HTTP-based RESTful protocol, HTML and Cascading Style Sheets for user interface integration, a choice of JSON or XML for data representation, and Atom for results. One of its goals is to facilitate interoperation between legacy health care systems, to make it easy to provide health care information to health care providers and individuals on a wide variety of devices from computers to tablets to cell phones, and to allow third-party application developers to provide medical applications which can be easily integrated into existing systems. FHIR provides an alternative to document-centric approaches by directly exposing discrete data elements as services. For example, basic elements of healthcare like patients, admissions, diagnostic reports and medications can each be retrieved and manipulated via their own resource URLs.

Figure 3A:
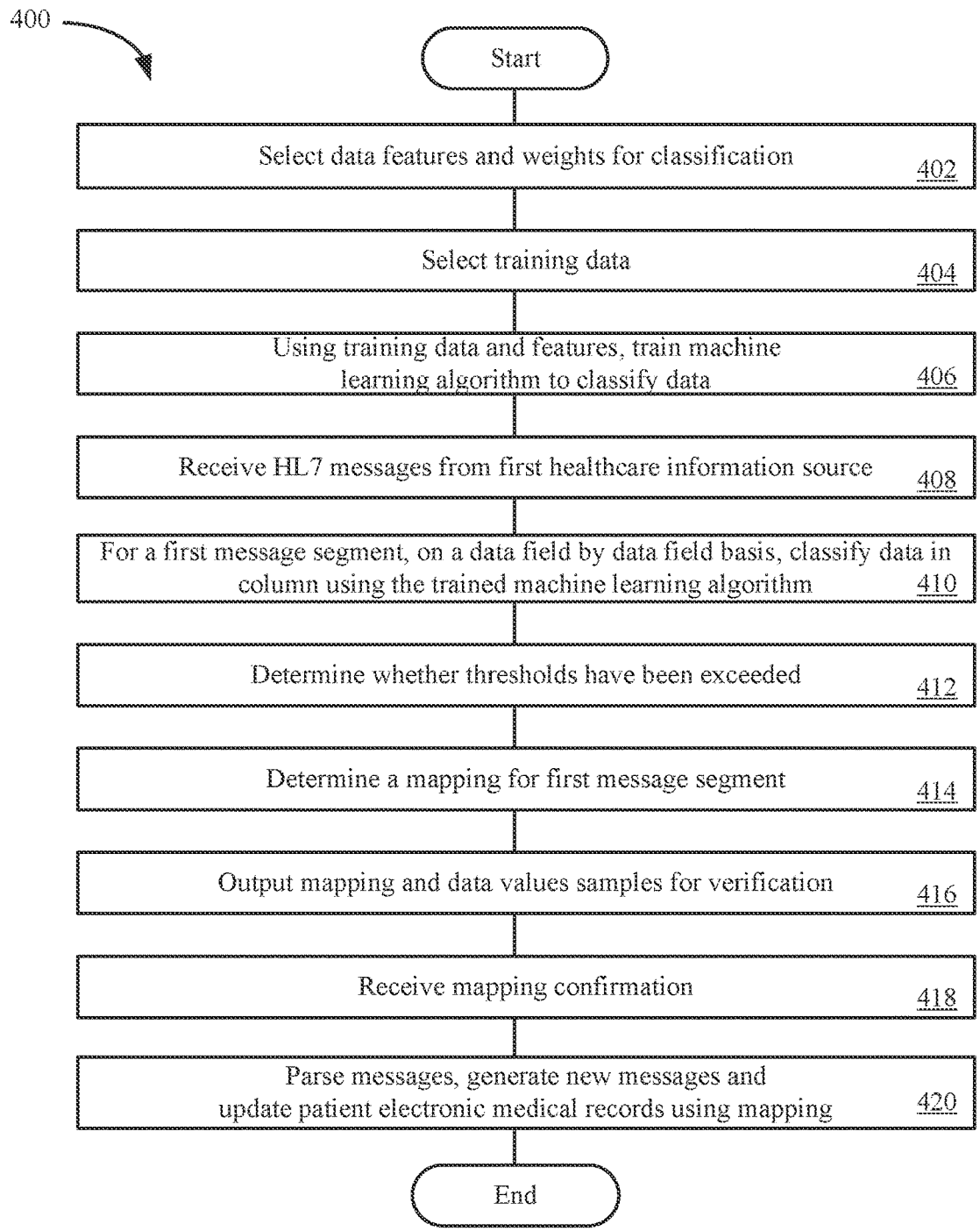
FIG. 3A illustrates a method of classifying information in an HL7 message using a machine learning algorithm in accordance with the described embodiments.
Figure 3B:
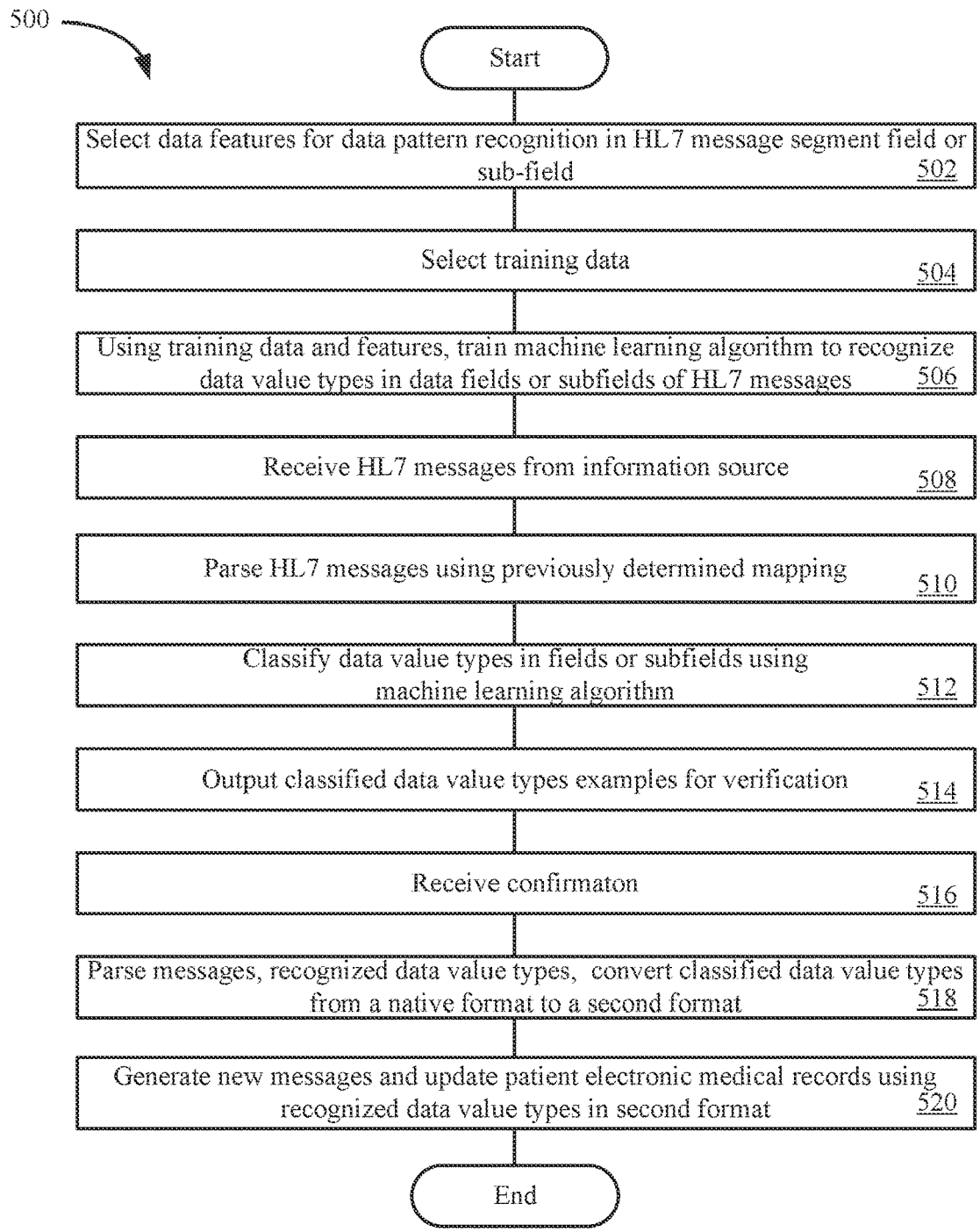
FIG. 3B illustrates a method of recognizing data patterns and transforming information in an HL7 message in accordance with the described embodiments.

Next, with respect to FIGS. 3A and 3B, methods of classifying data fields as particular data types and classifying data values within a classified data field into particular types of data values is described. The methods can utilize machine learning algorithms which are trained to perform the classifications. The methods can be applied to classifying data fields as particular data types in message segments from different healthcare information sources and then classifying the data values within a classified data field as a particular type of data value. The data values classified as a particular type of data value can be transformed from a first format to a second format.

FIG. 3A illustrates a method 400 of classifying data fields in a message segment from an HL7 message using a machine learning algorithm. In 402, data features, which can be used to characterize data values, can be selected. Examples of data features were describe above with respect to FIG. 2. In some instances, the values of the data features can be weighted when utilized by the machine learning algorithm. In 402, weights for the values of the data features can be selected.

In 404, a training data set can be selected. The training data set can include a plurality of data values each associated with a known data type. The training data can be culled from HL7 messages received at the HCS in FIG. 1. A training data set can be message segment specific because different message segments can utilize different data types in their data fields. For example, a first message segment can include a name or an address as a data type whereas a second message segment may not include the name or the address as a data type.

In 406, using the training data, data features and data feature weights (optional), a machine learning algorithm can be trained to classify data values in data fields of a message segment. An example of an application which can be used to train a machine learning algorithm is TensorFlow. TensorFlow is an open-source software library for dataflow programming across a range of tasks. It is a symbolic math library, and is also used for machine learning applications such as neural networks. Details of TensorFlow can be found at www.tensorflow.org Neural networks are computing systems vaguely inspired by the biological neural networks that constitute animal brains. Such systems "learn" (i.e. progressively improve performance on) tasks by considering examples, generally without task-specific programming. For example, in image recognition, they might learn to identify images that contain dogs by analyzing example images that have been manually labeled as "dog" or "no dog" and using the results to identify dogs in other images. Neural nets can perform this task without any a priori knowledge about dogs, such as they have fur, tails, whiskers and dog-like faces. Instead, they evolve their own set of relevant characteristics from the learning material that is processed.

A neural net is one example of a machine learning algorithm which can be utilized. Other examples of machine learning algorithms include decision trees, Naive Bayes classification, ordinary least square regression, logistic regression, support vector machines, ensemble methods, clustering algorithms, principal component analysis, singular value decomposition and independent component analysis. A decision tree is a decision support tool that uses a tree-like graph or model of decisions and their possible consequences, including chance-event outcomes, resource costs, and utility. Naive Bayes classifiers are a family of simple probabilistic classifiers based on applying Bayes' theorem with strong (naive) independence assumptions between the features. Least squares is a method for performing linear regression.

Logistic regression is a statistical way of modeling a binomial outcome with one or more explanatory variables. It measures the relationship between the categorical dependent variable and one or more independent variables by estimating probabilities using a logistic function, which is the cumulative logistic distribution. Support vector machines are a binary classification algorithm. Given a set of points of two types in N dimensional place, support vector machines generate a (N−1) dimensional hyperplane to separate those points into two groups.

Ensemble methods are learning algorithms that construct a set of classifiers and then classify new data points by taking a weighted vote of their predictions. The original ensemble method is Bayesian averaging, but more recent algorithms include error-correcting output coding, bagging, and boosting. Clustering is the task of grouping a set of objects such that objects in the same group (cluster) are more similar to each other than to those in other groups. Principal component analysis is a statistical procedure that uses an orthogonal transformation to convert a set of observations of possibly correlated variables into a set of values of linearly uncorrelated variables called principal components.

In linear algebra, singular value decomposition is a factorization of a real complex matrix. For a given m*n matrix M, there exists a decomposition such that M=UΣV, where U and V are unitary matrices and Σ is a diagonal matrix. Independent component analysis is a statistical technique for revealing hidden factors that underlie sets of random variables, measurements, or signals. Independent component analysis defines a generative model for the observed multivariate data, which is typically given as a large database of samples.

Depending on the machine learning algorithm, it can be trained using supervised or unsupervised learning. In supervised learning, the output datasets are provided which are used to train the machine and get the desired outputs whereas in unsupervised learning no datasets are provided, instead the data is clustered into different classes. In the examples of above, clustering algorithms, principle component analysis, singular value decomposition and independent component analysis are typically associated with unsupervised learning.

In 408, HL7 messages can be received from a first healthcare information source. The messages can be parsed into different message segments. In 410, for a first message segment, on a data field by data field basis, data values in each data field can be classified into data types associated with the first message segment using the trained machine learning algorithm. This process can repeated for a first plurality of HL7 messages from the first healthcare information source. In some instances, not every data field can include a data value. Further, the data fields which include data values can vary from HL7 message to HL7 message.

In one embodiment, the first message segment can be a personal identification (PID) message segment. However, data values from other types of message segments can be classified. Since the data types and number of data types can be different between message segments, a machine learning algorithm can be trained separately to classify each message segment. For example, a first training of a machine learning algorithm can be for classifying data values associated with a first message segment and a second training of the machine learning algorithm can be for classifying data values associated with a second message segment. The first training and the second training may involve providing separate training data sets, separate data feature sets and separate training weights.

The number of times data values in a data field have been classified and the data type which each data value has been classified can be tracked. In some instances, the trained machine learning algorithm may not be able to classify a data value. In addition, the trained machine learning algorithm may not classify a particular data value correctly. For instance, a street name called "John Doe Dr." could be classified as a patient name.

In 412, a determination can be made as to whether thresholds have been exceeded. A first threshold can be whether data values from a particular data field have been classified above a number of times, such as above one hundred times, above one hundred fifty times or above two hundred times. A second threshold can be whether data values have been classified as a particular data type above a certain percentage threshold. For example, the data values associated with a first data field may have been classified as a first data type 90% of the time by the trained machine learning algorithm or greater than 75% of the time.

In 414, a mapping can be determined for a first message segment. The mapping can specify a data type to each data field in the first message segment from a first healthcare information source. The mappings for each message segment can vary between different healthcare information sources. In 416, the mapping determined using the trained machine learning algorithm can be output, such as to a display, for verification from a human user. Data values which have been classified as a particular data type by the trained machine learning algorithm can be included. Using this information, a user can provide an input indicating that mapping is correct.

In 418, a mapping confirmation can be received. Alternately, input indicating needed changes to the mapping can be received and the mapping can be modified to reflect the input. For example, the input can indicate that a third data field in a first message segment is to be classified as a second data type instead of a first data type. In 420, HL7 messages can be parsed from the first healthcare information source and new messages to the first healthcare information source can be generated using the determined mapping. In addition, patient electronic medical records can be updated using information parsed from HL7 messages using the determined mapping.

FIG. 3B illustrates a method 500 of classifying data values in a classified data field in a message segment from an HL7 message using a machine learning algorithm. In this example, data value is assumed to be of a known data type. Thus, the classification can be whether the data value is a first type of data value or a second type of data value of the known data type. For example, the know data type can be a description of an allergy and the first type of data value can be a description of a first type of allergy and the second type of data value can be a description of a second type of allergy.

In 502, data features and weights to apply to the data feature values can be selected for data pattern recognition in HL7 message segment field or sub-field. In 504, training data can be selected to recognize the different types of data values. In some instances, the machine learning algorithm can be trained on a data field by data field basis. Thus, a first training of the machine learning algorithm can be to recognize first types of data values in a first data field and a second training of the machine learning algorithm can be to recognize second types of data values in a second data field. In 506, using the training data and selected data features, the machine learning algorithm can be trained to recognize data value types in data fields or subfields associated with message segments in HL7 messages.

In 508, as part of the training, HL7 messages can be received from a first healthcare information source. In 510, the HL7 messages can be parsed using the mapping determined in FIG. 3A. In 512, the different data pattern types can be classified as a particular type of data value in fields or sub-fields associated with a message segment.

In 514, classified data value types and examples of the classified data value types can be output for verification. In 516, a confirmation can be received that the data value types are being classified correctly. In 518, a HL7 message can be parsed, a data value within a field of a message segment can be recognized as a particular type of data value. Then, the particular type of data value can be converted from a first, native format to a second format. In 520, new HL7 messages can be generated and patient electronic medical records can be updated using the recognized data value types in the second format. An example of this conversion from a first format to a second format is described with respect to FIG. 7.

Next, with respect to FIGS. 4A-5B, some details of HL7 messages are described. As discussed above, the HL7 messages can include a plurality of different message segments. Each of the message segments can include different data fields. When a new healthcare information source is coupled to the healthcare clearinghouse system (HCS 5 in FIG. 1), the data fields in one or more of the message segments can be considered as unknown data types. Via receiving and parsing a plurality of the message segments, a trained machine learning algorithm can be used to classify the data values in each field as a particular data type. The classifications can be used to develop a mapping that is used to parse the HL7 messages from a healthcare information source.

FIG. 4A is a diagram of a HL7-ADT-A01 event message 200a. The A01 message is an admit/visit notification. In one embodiment, the HL7 ADT message, such as message 200a, can be used to transmit patient information. For example, patient identification information, patient contact information and patient insurance information can be sent from an electronic device at a medical practice to the HCS 5 as shown in FIG. 1.

The HL7 ADT message, such as message 200a, can be divided into a plurality of message segments where each message segment includes a number of different fields. A data value associated with a data type can be specified in each field. Some data fields can require a data value. Other data fields can optionally include a data value.

In more detail, the message 200a includes fourteen message segments. The fourteen message segments include MSH 202, EVN 204, PID 206, PD1 208, NK1 210, PV1 212, DB1 214, OBX 216, AL1 218, DG1 220, DRG 222, GT1 224, IN1 226, ACC 228 and UB1 230. Data fields 232, 234, 236, 238, 240, 242, 246, 248, 250, 252, 254, 256, 258 and 260 are associated with each of the message segments. The number of data fields in each of the data fields can vary from data field to data field.

The HL7 MSH (Message Header) segment 202 is usually present in every HL7 message type. It can define the message's source, purpose, destination, and certain syntax specifics like delimiters (separator characters) and character sets. The delimiters and character sets can be used to parse information from the message.

The data fields 232 of MSH segment 202 can include a field separator, encoding characters, a sending application, a sending facility, a receiving application, a receiving facility, a date/time of message, security, a message type, a message control id, a processing id, a version id, a sequence number, a continuation pointer, an accept acknowledgement type, an application acknowledgement type, a country code, a character set and a principal language of message.

The HL7 EVN (Event) segment 204 can be used to communicate trigger event information to receiving applications. The EVN segment 204 can include seven fields. The fields 234 can include an event type code, a recorded date/time, a date/time planned event, an event reason code, an operator id and an event occurred.

The HL7 PID (patient ID) message segment 306 can be used to communicate patient demographic information. It can be found every type of ADT (Admit Discharge Transfer) message. The PID message segment 206 can include thirty data fields 236. All or a portion of the fields can be specified in any message. Further, the fields which are specified can vary from message to message.

The fields 236 can include a set ID—patient ID, a patient ID (external ID), a patient ID (internal ID), an alternate Patient ID—PID, a patient name, a mother's maiden name, a date/time of birth, a sex, a patient alias, a race, a patient address, a country code, a phone number—home, a phone number—business, a primary language, a marital status, a religion, a patient account number, a SSN number—patient, a driver's license number—patient, a mother's identifier, an ethnic group, a birth place, a multiple birth indicator, a birth order, a citizenship, a veterans military status, a nationality, a patient death date and time and a patient death indicator.

As described above, the order of these data fields 236 can vary between different healthcare information sources. A trained machine learning algorithm can be configured to classify data values in each of the data fields as one of the thirty data types listed above. This process can be repeated for a plurality of messages and used to establish an order of the data types received in HL7 messages from a particular healthcare information source. This process can be implemented for different message segments. However, because the data types vary between message segments, the machine learning algorithm may be trained differently for each message segment.

The PD1 (Patient additional demographic) message segment 208 can include demographic information that is likely to change about the patient. It can include twenty one different fields 238. All or a portion of the fields can be specified and can vary from message to message. Some examples of the fields 238 include a living dependency, a living arrangement, a patient primary facility, a handicap, a living will code, an immunization registry status, a military branch and a military status.

The NK1 (Next of Kin/Associated Parties) message segment 210 can information about the patients other related parties. Any associated parties may be identified. Thus, multiple NK1 segments can be included in a message. It can include thirty nine different fields 240. All or a portion of the fields can be specified and can vary from message to message. Some examples of the fields 240 include a name, a relationship, an address, a phone number, a date of birth, a religion, an ethnic group, a contact reason and a VIP indicator.

The PV1 (Patient Visit Information) message segment 212 can be used to specify inpatient and outpatient encounter information. It can include fifty two different fields 242. All or a portion of the fields can be specified and can vary from message to message. Some examples of the fields 242 include an assigned patient location, an admission type, an attending doctor, a referring doctor, a consulting doctor, a diet type, a servicing facility and an admit date/time.

The DB1 (Disability) message segment 214 can contain information related to the disability of a person. This segment was created instead of adding disability attributes to each segment that contains a person (to which disability may apply). This is an optional segment that can be used to send disability information about a person. It can include eight different fields 244. All or a portion of the fields can be specified and can vary from message to message. The fields 244 can include an ID, disabled person code, a disabled person identifier, a disabled indicator, a disability start data, a disability end data, a disability return to work data and a disability unable to work date.

The OBX (Observation/Result) message segment 216 can be used to transmit a single observation or observation fragment. It can represent the smallest indivisible unit of a report. The OBX segment can also contain encapsulated data. It can include nineteen different fields 246. All or a portion of the fields can be specified and can vary from message to message. The fields 246 can include an ID, a value type, an observation identifier, an observation sub-ID, an observation value, units, reference ranges, abnormal flags, probability, nature of abnormal tests, observation result status, an effective date of the reference range, a user defined access checks, date/time of the observation, producer's ID, responsible observer, observation method, equipment instance identifier and data/time of the analysis.

In one embodiment, data values from an OBX message can be identified as a particular data value using a trained machine learning algorithm. Then, the particular data value can be transformed from a first format to a second format as described above with respect to FIG. 2. The format conversion can allow for observations to be described in a standard or common way across different healthcare information sources. This methodology can be applied to a data field in any of the message segments listed herein.

The AL1 (Patient Allergy Information) message segment 218 can contain patient allergy information of various types. Most of this information can be derived from user-defined tables. Each AL1 segment can describe a single patient allergy. Thus, multiple segments can be present. It can include six different fields 248. All or a portion of the fields can be specified and can vary from message to message. Some examples of the fields 248 include an ID, an allergen type code, an allergen description, an allergy severity code, an allergy reaction code and identification date.

The DG1 (Diagnosis) message segment 220 can contains patient diagnosis information of various types, for example, admitting, primary, etc. The DG1 segment is used to send multiple diagnoses (for example, for medical records encoding). It can include twenty one different fields 220. All or a portion of the fields can be specified and can vary from message to message. Some examples of the fields 250 include an ID, a diagnosis coding method, a diagnosis description, a diagnosis date/time, a diagnosis type, a diagnosing clinician and a diagnosis action code.

The DRG (Diagnosis related Group) message segment 222 can contain diagnoses-related grouping information of various types. The DRG segment is used to send the DRG information, for example, for billing and medical records encoding. It can include eleven different fields 252. All or a portion of the fields can be specified and can vary from message to message. Some examples of the fields 252 include a diagnostic related group, a DRG assigned date/time, a DRG approval indicator, a DRG grouper review code, an outlier type, outlier days, outlier cost, a DRG payer, an outlier reimbursement, confidential indicator and a DRG transfer type.

The GT1 (Guarantor) message segment 224 can include guarantor data for patient and insurance billing applications (e.g., the person or the organization with financial responsibility for payment of a patient account). This GT1 message segment can include fifty five fields 254. All or a portion of the fields can be specified and can vary from message to message.

The fields 254 can include guarantor number, guarantor name, guarantor spouse name, guarantor address, guarantor phone number-home, guarantor phone number-business, guarantor date/time of birth, guarantor sex, guarantor type, guarantor relationship, guarantor SSN, guarantor date—begin, guarantor date—end, guarantor priority, guarantor employer name, guarantor employer address, guarantor employer phone number, guarantor employee id number, guarantor employment status, guarantor organization name, guarantor billing hold flag, guarantor credit rating code, guarantor death date and time, guarantor death flag, guarantor charge adjustment code, guarantor household annual income, guarantor household size, guarantor employer id number, guarantor marital status code, guarantor hire effective date, employment stop date, living dependency, ambulatory status, citizenship, primary language, living arrangement, publicity code, protection indicator, student indicator, religion, mother s maiden name, nationality, ethnic group, contact persons' name, contact persons' telephone number, contact reason, contact relationship, job title, job code/class, guarantor employer s organization name, handicap, job status, guarantor financial class and guarantor race.

The IN1 (insurance) message segment 226 can include insurance policy coverage information necessary to produce properly pro-rated and patient and insurance bills. The segment 226 can include forty nine fields 256. All or a portion of the fields can be specified and can vary from message to message.

The fields 256 can include set ID—patient ID, insurance plan ID, insurance company ID, name of insured, insured's relationship to patient, insured's date of birth, insured's address, insurance company name, insurance company address, insurance co contact person, insurance co phone number, group number, plan effective date, group name, insured's group employer id, insured's group employee name, plan expiration date, authorization information, plan type, name of insured, insured's relationship to patient, insured's date of birth, insured's address, assignment of benefits, coordination of benefits, coordination of benefit priority, notice of admission flag, notice of admission date, report of eligibility flag, report of eligibility date, release information code, pre-admit certification, verification date/time, verification by, type of agreement code, billing status, lifetime reserve days, delay before lifetime reserve day, company plan code, policy number, policy deductible, policy limit—amount, policy limit—days, room rate—semi-private, room rate—private, insured's employment status, insured's sex, insured's employer's address, verification status, prior insurance plan id, coverage type, handicap and insured's ID number.

The ACC (Accident) message segment 228 can contain patient information relative to an accident in which the patient has been involved. This ACC message segment can include eleven fields 258. All or a portion of the fields can be specified and can vary from message to message. The fields 258 can include an accident time/date, an accident code, an accident location, an auto accident state, an accident job related indicator, an entered by, an accident description, a brought in by, a police notified indicator and an accident address.

The UB1 (UB82) message segment 230 can contain the data necessary to complete UB82 bills specific to the United States; other realms may choose to implement using regional code sets. This UB1 message segment can include twenty three fields 260. All or a portion of the fields can be specified and can vary from message to message. Examples of the fields 260 can include an ID, a blood deductible, blood furnished, blood replaced, co-insurance days, covered days, non-covered days, occurrence and an occurrence span.

FIG. 4B is a diagram of a HL7-ADT-A02 event message 200b. Message 200b is used to transfer a patient. The message 200b includes a subset of the message segments in message 200a. HL7 version 2.5 defines sixty two different types of messages. In many instances, the messages include a subset of the data types and data fields shown in event message 200a.

In other instances, an HL7 message can include a subset of the data types and data fields shown in event message 200a and additional data types and data fields. In FIG. 4C, a diagram of an HL7-ADT-A43 message 200c shown. It is a move patient message. It includes four message segments shown in messages 200a and 200b. In addition, it includes an MRG message segment 235 including fields 262. The MRG (merge patient) message segment 235 can provide receiving applications with information necessary to initiate the merging of patient data as well as groups of records. It can include seven fields, such as prior patient identification list, a prior alternate patient ID, a prior patient account number, a prior patient ID, a prior visit number, a prior alternate visit ID and a prior patient name.

FIG. 4D is an example of a HL7-ADT-A01 message. The message segments include a MSH segment 202a, an EVN segment 204a, a PID message segment 206a, a NK1 message segment 210a, a PV1 message segment 212a, GT1 message segment 224a, a DG1 message segment 220a, a first insurance segment (IN1) 226a and a second insurance (IN2) segment 226b. The message segments are a subset of the message segments listed in FIG. 4A.

The data fields in each message segment are separated by the pipe character, "|." The data field, subfields, are separated by the caret character, "^." The MSH segment 202a includes fourteen data fields of which nine have values. The EVN message segment 204a includes six data fields of which two have values. The PID message segment 206a includes twenty eight data fields of which sixteen have values. The NK1 message segment 210a includes nineteen data fields of which six have values. The PV1 message segment 212a includes forty seven data fields of which fourteen have values. The GT1 message segment 224a includes twenty data fields of which thirteen have values. The DG1 message segment 220a includes six data fields of which five have values. The IN1 message segment 226a and IN2 message segment 226b each include forty six message data fields. Sixteen of the fields are populated for segment 226a and six are populated for segment 226b.

The number of data fields in each message segment in the example can be different than the number of data fields described with respect to FIG. 4A. In FIG. 4A, the number of data fields was described for HL7 version 2.5 whereas in FIG. 4D, the example is associated with version 2.3. The version number is indicated in the MSH segment 202a. The number of data fields in a message segment can vary from HL7 version number to HL7 version number. Thus, when HL7 messages are classified from a healthcare information source, it is possible that the messages may not include a data field which is included in a later version.

The MSH segment 202a can include information such as the message type, which is an "ADT-A01" message and the version number which is 2.3. The EVN message segment 204a also indicates the message is an "A01" message. The PID message segment 206a includes information such as a name and address of a patient. The fields include sub-fields as indicated by the caret character.

As described above, the number of subfields in a field can be a data feature used by a trained machine learning algorithm. The number of subfields can be determined from the caret character. Further, as described above, the position of the data value in the data field can be a data feature. For example, in the PID message segment, the field with the name, "John D. Doe," includes three subfields and is in the sixth position.

The NK1 message segment 210a includes the name of a related person and an address. The PV1 message segment 212a includes information related to the visit, such that it is a preoperative visit. The GT1 message segment 224a includes the name and address of the patient. The patient is also a guarantor for payment of the bill.

The DG1 message segment 220a includes information about the diagnosis which is associated with osteoarthritis in the leg. The first insurance message segment 226a indicates the insurance is Medicare. The second insurance information in segment 226b is associated with the company, "Deersrus, Inc."

Next, an ORM event message is described. The ORM message can be used to order a number of different medical tests. FIG. 5A is a diagram of a HL7 ORM-001 event message 200d. The message 200d is shown with thirteen message segments including MSH 202, NTE 264, PID 206, NTE-1 266, PV1 208, AL1 218, ORC 268, OBR 270, DG1 220, OBX 216, CTI 272 and BLG 274. The message segments can be associated with fields 232, 276, 236, 278, 238, 256, 248, 280, 282, 250, 246, 284 and 286, respectively.

The NTE (Notes and comments) message segment 266 can be used to send notes and comments in a message, such as notes and comments about a medical test. It can include fields 278 such as set ID-NTE, source of comment, comment and comment type. The NTE-1 message segment 266 and fields 278 can specify additional notes and comments. The comment is limited in length. Thus, the NTE message segment can be repeated a number of times.

The ORC (common order) message segment 268 can be used to specify can be used to transmit fields that are common to all orders (all types of services that are requested). The ORC segment can be required in the Order (ORM) message. ORC can be mandatory in Order Acknowledgment (ORR) messages if an order detail segment is present, but may not be required otherwise. The ORC segment 268 can be repeated in a message, such as to specify multiple orders of medical tests.

The ORC message segment 268 can include thirty-one fields 280. All or a portion of the fields can be specified and can vary from message to message. The filler can be the entity which fulfills a medical test described in the order. The fields 280 can include order control, placer order number, filler order number, placer group number, order status, response flag, quantity/timing parent order, date/time of transaction, entered by, verified by, ordering provider, enterer's location, call back phone number, order effective date/time, order control code reason, entering organization, entering device, action by, advanced beneficiary notice code, ordering facility name, ordering facility address, ordering facility phone number, ordering provider address, order status modifier, advanced beneficiary notice override reason, filler's expected availability date/time, confidentiality code order type, enterer authorization mode and parent universal service identifier.

The OBR message segment 270 can be used to transmit information about an exam, diagnostic study/observation, or assessment that is specific to an order or result. In an ORM message, the OBR segment 270 can be part of an optional group that provides details about the order. The OBR segment can include forty three fields 282, such as set ID-OBR, placer order number, filler order number, universal service ID, requested date/time, collection volume, collector identifier, specimen action code, relevant clinical information, specimen received date/time, ordering provider, order callback phone number, reason for study, technician scheduled date/time number of sample containers, transport logistics of collected sample, etc.

The CTI (Clinical Trial Identification) message segment 272 can be an optional segment that includes information to identify the clinical trial, phase and time point with which an order or result is associated. The message segment 272 can include three fields 284. The three fields 284 can include sponsor study ID, study phase identifier and study scheduled time point.

The BLG (Billing) message segment 274 can be used to provide billing information, on the ordered service, to the filling application. As described in FIG. 1, the medical test order clearinghouse module 16 at the HCS 5 after receiving the ORM message can parse and then notify a filling application at the medical testing services 25a or 25b. The billing message segment can include three fields 286 including when to charge, charge type and account ID.

Next, an example of an HL7 ORM event message is described with respect to FIG. 5B. Again, the pipe character, "|," are used to separate fields. A space between two vertical lines indicates no value is specified for a field. The control characters 302 specify control characters used to encode the message. Different control characters can be used to parse the message and thus, can be interpreted by a message parser.

This format is provided for illustration purposes only. In other versions of HL7, XML encoding can be used (Version 3). Further, different control characters can be specified. In this example, the caret symbol can be used as a component separator in a field. The ampersand can be used as a subcomponent separator. The tilde can be used as field repeat separator. The back slash can be used as an escape character.

The sending application 304 is a healthcare application system (HIS). The sending facility 306 is a medical practice, called practice. The receiving application 308 is a laboratory information system associated with a medical testing service. The receiving facility 310 is identified as "Lab." The date and time 312 of the message is called "Date-Time." It can be a series of numbers indicating date and time the message was generated.

The message control ID 316 can be a unique identifier associated with the message. It can be a series of numbers. The version number 318 can be the version number of HL7 which was used to encode the message.

The patient ID 320 can be a unique patient identification number. It can be a combination of letters and/or numbers. The patient name 322 is referred to as "Mr. John Doe." The DOB 324 is the date of birth of the patient. The carets with no data between them refer to components which can be specified, but are unspecified. The date of birth 324 can be a series of numbers. The gender 326 can be a letter, such as M or F. The address 328 can be an address of the patient and can include numbers and letters.

The patient location 330 can be a facility where the patient is located, such as a name of a medical practice. The admission type 332 can referred to an inpatient or outpatient service. The referring doctor 334 can be a name of a doctor that referred the patient. An alternate visit ID 336 can be an additional identifier assigned to the patient visit. It can be a series of numbers and/or letters.

The order control 338 can indicate a type of order. For example, NW refers to a new order. The placer order number 340 and filler order number 342 can be numbers assigned by the placer and filler respectively to the order. The call back number 344 can be a phone number which can be used to contact the placer and get additional information about the order. The data field 346 specifies information about an ordered test, which is a urinalysis.

Next, with respect to FIGS. 6 and 7, an example of mapping a message segment and an example of transforming a data value type from a first format to a second format are described. FIG. 6 illustrates an example 600 of a mapping of HL7 messages using a trained machine learning algorithm. Based upon the mapping, a message translator can be generated for a healthcare information source in a healthcare network.

In the example 600, a PID message segment is mapped based on data values from a plurality of HL7 messages from a healthcare information source. The machine learning algorithm can be trained to recognize all or portion of the fields associated with the PID message segment. In this example, thirty fields that can be associated with a PID message segment are shown. Other types of message segments can be mapped from a healthcare information source and the PID message segment is provided for the purposes illustration only.

In 600, three columns are shown. The first column 605 lists positions in a data field associated with the message segment. The zero position is associated with the message segment identifier which is "PID." The second column, referred to HCS Format 607, lists thirty known data types associated with a PID message segment in a first order utilized by the HCS 5 (see FIG. 1). The third column is referred to as healthcare information source 609. In the third column, a second order of the known data types from the second column is obtained using a trained machine learning algorithm to classify data values from the PID message segments in a plurality HL7 messages received from the healthcare information source.

The data types and the order utilized by the HCS 5 can be consistent with a particular HL7 version, such as HL7 version 2.5. In one embodiment, the order can be used to construct an HL7 message with a PID message segment that is sent from the HCS 5. In the second column, the known data types are provided in the following order associated with positions one through thirty: the patient ID 604a, external ID 606a, internal ID 608a, alternate patient ID 610a, patient name 612a, mother's maiden name 614a, date of birth 616a, sex 618a, patient alias 620a, race 622a, address 624a, country code 626a, phone number 628a, phone number 630a, primary language 632a, marital status 634a, religion 635a, patient account number 636a, SSN 638a, driver's license number 640a, mothers identifier 642a, ethnic group 644a, birth place 646a, multiple birth indicator 648a, birth order 650a, citizenship 652a, veterans military status 654a, nationality 656a, patient death date and time 658a and patient death indicator 660a.

In the third column, the External ID 606b is determined to be in the first position by trained machine learning algorithm as compared to the second position in the second column. The patient ID 604b is determined to be in the second position as compared to the first position in the second column. The internal ID 608b, the patient name 612b, the date of birth 616b, sex 618b, race 622b, address 624*b*, phone number 628*b*, phone number 630*b* and primary language 632*b* are classified by the trained machine learning algorithm as being in the third, fifth, seventh, eighth, tenth, eleventh, thirteenth, fourteenth and fifteenth positions, respectively. These positions are the same as the positions of these values in the second column associated with the HCS 5.

In the third column, the religion 634*b* is determined to be in the sixteenth position by trained machine learning algorithm as compared to the seventeenth position in the second column. The marital status 635 is determined to be in the seventeenth position as compared to the sixteenth position in the second column. The SSN 638*b* and the ethnic group 644*b* are determined by the trained machine learning algorithm to be in the nineteenth and twenty second positions which is the same positions as in the second column.

In one embodiment, the classifier can be configured to receive verification of the order in the third column by a human operator. Then, the order can be used to parse the PID message segment in HL7 messages received the healthcare information source. Information parsed from the messages can be used to update patient EMRs at the HCS 5.

The alternate patient ID, the mother's maiden name, the patient alias, the country code, the patient account number, the driver's license number, mother's identifier, birth place, multiple birth indicator, birth order, citizenship, veterans military status, nationality, patient death date and time and patient death indicator have not been classified by the trained machine learning algorithm. In some instances, the messages from the healthcare information source may not include data values in one of the fields of data. In another instance, the data values may only be included infrequently.

In the instances, when a field is not classified. The system can attempt to assign the field based upon its position. For example, position eighteen in the third column can be classified as the patient account number, which is the data type associated with the second column. The system can also be considered to receive a verification of this classification.

Next, an example of classifying a data value in a field of a known data type as a particular type of data value within the field is described. FIG. 7 illustrates an example of transforming a data value in a data field within a message segment from HL7 messages using a trained machine learning algorithm. Details of the method are described above with respect to FIG. 2

A data field in the message segment can be classified as a particular data type. As described above, a first machine learning algorithm can be trained to classify data values as a particular data type. Then, a second machine learning algorithm can be configured to classify data values within a particular data type as a particular data value type. In 702, examples of particular data value type, which describes a blood pressure measurement, are shown.

The examples include "Blood Pressure High," "High BP," "BP High," "Blood Pressure is H," "BP H," and "BP is High." The trained machine learning algorithm can classify all of these data values as being associated with a data value type that describes blood pressure is being high. After each example is classified, it can be transformed into a standardized data pattern 704. For example, the examples can each be transformed to the description "Blood Pressure is High 706."

In one embodiment, the transformed description can be stored to a patient EMR, such as EMR 708. Further, the transformed description can be used when new HL7 messages are generated 710. One benefit of using a common description format is that it may reduce the likelihood of medical errors as compared to describing the same phenomena many different ways.

In another embodiment, machine learning can be used to determine when to update reports. As an example, a doctor can order three panels for a blood test, such as a CBC (complete blood count), a (CMP) comprehensive metabolic panel and a thyroid test. The tests can be performed and blood can be sent to a laboratory. The laboratory can perform a portion of the tests, such as the CBC and the CMP and send the results in a preliminary report.

The thyroid test can be performed 1-2 days later. After the thyroid test is complete, the laboratory can be configured to send an updated report. The updated report can contain the entire report (all the tests in the panel) or it can contain on the thyroid panel tests. When only the thyroid tests are sent in the update, the system can be configured to add those to the previous report. When the lab sends the entire report with results from all tests, the system can be configured to replace the entire report with a new complete report.

The update rules can be unique to each laboratory information system. A machine learning algorithm can be trained to receive reports from a laboratory and determine whether the update is a partial update or a new complete report. Further, the machine learning algorithm can be configured to determine the tests described in the report. Based upon this classification, the machine learning algorithm can be used to classify reports associated with different combinations of tests and determine when the laboratory is incrementally or completely updating the report in accordance with the test combination. Once the rules are determined, code can be generated that determines when to append or replace a report.

Embodiments of the present invention further relate to computer readable media that include executable program instructions. The media and program instructions may be those specially designed and constructed for the purposes of the present invention, or any kind well known and available to those having skill in the computer software arts. When executed by a processor, these program instructions are suitable to implement any of the methods and techniques, and components thereof, described above. Examples of computer-readable media include, but are not limited to, magnetic media such as hard disks, semiconductor memory, optical media such as CD-ROM disks; magneto-optical media such as optical disks; and hardware devices that are specially configured to store program instructions, such as read-only memory devices (ROM), flash memory devices, EEPROMs, EPROMs, etc. and random access memory (RAM). Examples of program instructions include both machine code, such as produced by a compiler, and files containing higher-level code that may be executed by the computer using an interpreter. The media including the executable program instructions can be executed on servers or other computation devices including processors and memory.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed is:

1. A method in an electronic healthcare system including a plurality of health care information sources comprising:
receiving a first plurality of HL7 messages from a first healthcare information source wherein each of the first plurality of HL7 messages includes a plurality of HL7 message segments;
parsing the first plurality of HL7 messages to identify a patient identification (PID) message segment among the HL7 message segments wherein the PID message segment includes a plurality of data types each associated with a data field in the PID message segment and wherein an order of the plurality of data types in the PID message segment from the first healthcare information source is unknown;
for each of the data fields in the PID message segment in each of the first plurality of HL7 messages, i) determining whether a data value is present; ii) when the data value is present, using the data value to determine a plurality of values of data features wherein the data features characterize the data value and wherein the plurality of values of the data features are used by a trained machine learning algorithm to classify the data value as one of the plurality of data types and iii) based upon the plurality of values of the data features, classifying using the trained machine learning algorithm the data value as one of the plurality of data types in the PID message segment wherein the trained machine learning algorithm is used to determine how to correctly parse the HL7 messages from the first healthcare information source; and
for a first data field in the PID message segment in the first plurality of messages from the first healthcare information source, i) determining the first data field is classified as one of the plurality of data types a first number of times wherein the first number of times exceeds a first threshold value, ii) determining the first data field is classified as a first data type among the plurality of data types a percentage of the first number of times wherein the percentage exceeds a second threshold value and iii) determining a first position of the first data field in the PID message segment.

2. The method of claim 1, wherein the trained machine learning algorithm is selected from among the group consisting of a neural net, a decision tree, a naive Bayes classifier, ordinary least squares regression, a logistic regression, a support vector machine, an ensemble method, a clustering algorithm, a principal component, a singular value decomposition and an independent component analysis.

3. The method of claim 1, wherein the data features are selected from the group consisting of a total number of letters in the data value, a total number of numbers in the data value, a ratio between the total number of letters to the total number of numbers in the data value, a total number of characters in the data value, a total number of sub-fields in each data field, a position number in the data fields of the PID message segment, an N-gram, a cosine similarity, a Jaccard similarity, a Levenshtein distance and a feature hashing.

4. The method of claim 1, wherein the first threshold value is greater than one hundred.

5. The method of claim 1, where the second threshold value is greater than ninety percent.

6. The method of claim 1, wherein the plurality of data types is selected from the group consisting of a patient ID, an External ID, a patient name, a date of birth, a sex, an address, a phone number, a primary language, a marital status and a social security number.

7. The method of claim 1, wherein the plurality of data types is selected from the group consisting of an alternate patient ID, a mother's maiden name, a race, a country code, a religion, a driver's license number, a birth place, multiple birth indicators, a citizenship, a veteran's military status, a nationality, a patient death data and time and a patient death indicator.

8. The method of claim 1, further comprising generating a HL7 message for a second healthcare information source wherein the HL7 message includes the PID message segment and wherein the first data field associated with the first data type in the PID message segment is in a second position different from the first position.

9. The method of claim 1 further comprising:
receiving a second plurality of HL7 messages from the first information source including the PID message segment;
parsing the PID message segment in the second plurality of HL7 messages using the first position of the first data field determined using the trained machine learning algorithm to determine first data values of the first data field associated with the first data type; and
updating electronic medical records in a healthcare information database using the first data values from the first data field associated with the first data type parsed from the second plurality of HL7 messages.

10. The method of claim 9, prior to parsing the PID message segment in the second plurality of HL7 messages, outputting the first position of the first data field and the first data type determined using the trained machine learning algorithm, outputting example values associated with the first data field and receiving an input indicating the first data type is correct.

11. The method of claim 9, further comprising:
receiving a third plurality of HL7 messages from a second healthcare information source wherein each of the third plurality of HL7 messages includes the plurality of HL7 message segments;
parsing the third plurality of HL7 messages to identify the patient identification (PID) message segment among the HL7 message segments wherein a second order of the plurality of data types in the PID message segment from the second healthcare information source is unknown;
for each of the data fields in the PID message segment in each of the third plurality of HL7 messages, i) determining whether the data value is present; ii) when the data value is present, using the data value to determine the plurality of values of data features wherein the data features characterize the data value and iii) based upon the plurality of values of the data features, classifying using the trained machine learning algorithm the data value as one of the plurality of data types in the PID message segment;

classifying, using the trained machine learning algorithm, a second data field in a second position of the PID message segment in the third plurality of messages from the second healthcare information source as the first data type.

12. The method of claim 11, wherein the first position and the second position are in a different position in the PID message segment for the first healthcare information source and the second healthcare information source.

13. The method of claim 1, further comprising training the machine learning algorithm to classify the plurality of data types in the PID message segment using the data features.

14. The method of claim 13, wherein the data features are weighted during the training of the machine learning algorithm.

15. The method of claim 1, further comprising:
for a second data field in the PID message segment in the first plurality of messages from the first healthcare information source, i) determining the second data field is classified as one of the plurality of data types the first number of times wherein the first number of times exceeds a third threshold value, ii) determining the second data field is classified as a second data type among the plurality of data types the percentage of the first number of times wherein the percentage exceeds a fourth threshold value and iii) determining a second position of the second data field in the PID message segment; and
parsing the PID message segment in the second plurality of HL7 messages using the second position of the second data field determined using the machine learning algorithm to determine second values of the second data field associated with the first data type.

16. The method of claim 15 wherein the third threshold value is equal to the first threshold and wherein the fourth threshold is equal to the second threshold.

17. The method of claim 1, further comprising
parsing the first plurality of HL7 messages to identify a second message segment among the HL7 message segments wherein the second message segment includes a second plurality of data types each associated with one of the data fields in the second message segment and wherein an order of the second plurality of data types in the second message segment from the first healthcare information source is unknown;
for each of the data fields in the second message segment in each of the first plurality of HL7 messages, i) determining whether the data value is present; ii) when the data value is present, using the data value to determine a plurality of values of second data features wherein the plurality of values of the second data features are used by the trained machine learning algorithm to classify the data value as one of the second plurality of data types and iii) based upon the plurality of values of the second data features, classifying using the trained machine learning algorithm the data value as one of the second plurality of data types in the second message segment.

18. A method in an electronic healthcare system including a plurality of health care information sources comprising:
receiving a first plurality of HL7 messages from a first healthcare information source wherein each of the first plurality of HL7 messages includes a plurality of HL7 message segments;
parsing the first plurality of HL7 messages to identify a first message segment among the HL7 message segments wherein the first message segment includes a plurality of data types each associated with a data field in the first message segment and wherein an order of the plurality of data types in the first message segment from the first healthcare information source is unknown;
for each of the data fields in the first message segment in each of the first plurality of HL7 messages, i) determining whether a data value is present; ii) when the data value is present, using the data value to determine a plurality of values of data features wherein the data features characterize the data value and wherein the plurality of values of the data features are used by a trained machine learning algorithm to classify the data value as one of the plurality of data types and iii) based upon the plurality of values of the data features, classifying using the trained machine learning algorithm the data value as one of the plurality of data types in the first message segment wherein the trained machine learning algorithm is used to determine how to correctly parse the HL7 messages from first information source; and
for a first data field in a first position of the first message segment in the first plurality of messages from the first healthcare information source, determining the first data field is classified as a first data type.

19. The method of claim 18 further comprising:
receiving a second plurality of HL7 messages from the first information source including the first message segment; and
parsing the first message segment in the second plurality of HL7 messages using the first position of the first data field determined using the trained machine learning algorithm to determine first values of the first data field associated with the first data type.

20. The method of claim 18, wherein the first message segment is a patient identification message segment.

* * * * *